US010533978B2

(12) United States Patent
Benke et al.

(10) Patent No.: US 10,533,978 B2
(45) Date of Patent: *Jan. 14, 2020

(54) VIBRATION SENSOR ASSEMBLY FOR PROGNOSTIC AND DIAGNOSTIC HEALTH ASSESSMENT OF A POWER CIRCUIT BREAKER'S POWER TRANSMISSION AND DISTRIBUTION SYSTEM IN REAL TIME

(71) Applicant: Eaton Corporation, Cleveland, OH (US)

(72) Inventors: James Jeffery Benke, Pittsburgh, PA (US); Koustubh Dnyandeo Ashtekar, Moon Township, PA (US); Li Yu, Pittsburgh, PA (US); Jiong Chen, Shanghai (CN); Fangji Wu, Shanghai (CN); He Yang, Shanghai (CN); Wilbert deVries, Suzhou (CN)

(73) Assignee: EATON INTELLIGENT POWER LIMITED, Dublin (IE)

( * ) Notice: Subject to any disclaimer, the term of this patent is extended or adjusted under 35 U.S.C. 154(b) by 245 days.

This patent is subject to a terminal disclaimer.

(21) Appl. No.: 14/825,219

(22) Filed: Aug. 13, 2015

(65) Prior Publication Data

US 2017/0045481 A1  Feb. 16, 2017

(51) Int. Cl.
*G01H 1/00* (2006.01)
*G01N 29/14* (2006.01)
(Continued)

(52) U.S. Cl.
CPC .............. *G01N 29/46* (2013.01); *G01H 1/00* (2013.01); *G01N 29/14* (2013.01);
(Continued)

(58) Field of Classification Search
CPC ......... H01H 11/0062; H01H 2071/044; H01H 2071/042; H01H 2071/048; H01H 71/04;
(Continued)

(56) References Cited

U.S. PATENT DOCUMENTS 4,975,800 A * 12/1990 Oshita ................ G01R 31/3274
324/520
5,107,447 A * 4/1992 Ozawa ................ G01R 15/142
324/536
(Continued)

FOREIGN PATENT DOCUMENTS

CN  202631704 U  * 12/2012

OTHER PUBLICATIONS

Houser et al, Vibration Signal Analysis Techniques, 1973.*
(Continued)

*Primary Examiner* — Daniel S Larkin
*Assistant Examiner* — David L Singer
(74) *Attorney, Agent, or Firm* — Eckert Seamans

(57) ABSTRACT

A component monitoring system structured to monitor circuit breaker assembly component characteristics is provided. The component monitoring system includes a record assembly, a number of vibration sensor assemblies, a comparison assembly, and an output assembly. The record assembly includes selected nominal data for a selected circuit breaker component. The vibration sensor assembly is structured to measure a number of actual component characteristics for a substantial portion of the circuit breaker assembly and to transmit actual component characteristic output data. The comparison assembly is structured to receive an electronic signal from said record assembly and said sensor assemblies, to compare each sensor assembly actual component characteristic output data to said selected nominal data and to provide an indication signal as to whether said sensor assembly output data is acceptable when compared to the selected nominal data. The output assembly includes a communication assembly and an output device.

2 Claims, 20 Drawing Sheets

(51) Int. Cl.
*G01N 29/44* (2006.01)
*G01N 29/46* (2006.01)
*H01H 71/04* (2006.01)
*G01R 31/327* (2006.01)
*H01H 1/00* (2006.01)

(52) U.S. Cl.
CPC ......... *G01N 29/4427* (2013.01); *H01H 71/04* (2013.01); *G01N 29/4418* (2013.01); *G01N 2291/023* (2013.01); *G01N 2291/0289* (2013.01); *G01R 31/3274* (2013.01); *G01R 31/3277* (2013.01); *H01H 1/0015* (2013.01); *H01H 2071/044* (2013.01)

(58) Field of Classification Search
CPC ......... H01H 1/0015; H01H 2003/3073; H01H 2300/052; G01R 31/3274–3275; H02H 1/0023; H02H 3/04; H02H 3/044; G01N 29/4409; G01N 29/4418; G01N 29/4427; G01N 29/46; G01N 29/445; G01N 29/48; G01N 29/449; G01N 29/4445; G01H 17/00; G01H 1/00; G01H 1/04–08; G01H 1/12–16; G06F 11/008; G06F 11/0754
USPC ........... 200/308; 324/424, 765.01; 335/6–46, 335/167–176; 702/34, 181, 183–185, 60; 73/579, 649
See application file for complete search history.

(56) References Cited

U.S. PATENT DOCUMENTS

| | | | | | |
|---|---|---|---|---|---|
| 5,419,197 | A * | 5/1995 | Ogi | ................... | G05B 23/0221 702/141 |
| 5,629,869 | A * | 5/1997 | Johnson | ............. | H01H 11/0062 361/88 |
| 5,726,367 | A * | 3/1998 | Patel | ........................ | G01D 9/38 73/865.9 |
| 6,215,408 | B1 * | 4/2001 | Leonard | ............. | G01R 31/3274 324/415 |
| 6,242,708 | B1 * | 6/2001 | Marchand | .......... | H01H 33/6661 218/153 |
| 6,286,377 | B1 * | 9/2001 | Benke | ................ | H01H 11/0062 73/865.9 |
| 6,687,654 | B2 * | 2/2004 | Smith, Jr. | .......... | G05B 23/0235 702/183 |
| 6,912,484 | B2 * | 6/2005 | Bibelhausen | ...... | G05B 23/0216 702/183 |
| 8,456,259 | B2 * | 6/2013 | Safreed, III | ............. | H01H 9/20 200/330 |
| 2003/0216888 | A1 * | 11/2003 | Ridolfo | .............. | G05B 23/0283 702/181 |
| 2007/0252667 | A1 * | 11/2007 | Zhou | ..................... | H01H 3/227 335/16 |
| 2008/0296137 | A1 * | 12/2008 | Chen | .................... | H01H 3/3005 200/400 |
| 2008/0296138 | A1 * | 12/2008 | Chen | ...................... | H01H 71/44 200/400 |
| 2009/0109021 | A1 * | 4/2009 | Paoletti | ................ | G01R 31/343 340/540 |
| 2014/0055886 | A1 * | 2/2014 | Spangenberg | ......... | H01H 33/26 361/2 |
| 2014/0069195 | A1 * | 3/2014 | Ledbetter | ............... | G01H 17/00 73/649 |
| 2014/0090965 | A1 * | 4/2014 | Leccia | ............... | G01R 31/3274 200/308 |
| 2014/0149806 | A1 * | 5/2014 | Khalastchi | ......... | G06K 9/00496 714/49 |

OTHER PUBLICATIONS

MacMillan Dictionary, definition of subtantially.*
Merriam-Webster Dictionary, definition of substantial.*
Cambridge Dictionary, definition of substantially.*
Bryhn et al, An Operational Definition of a Statistically Meaningful Trend, Apr. 28, 2011.*
Dictionary.com, definition of efficacy.*
Merriam-Webster Dictionary, definition of like new.*
Machine translate CN202631704U.*
Federal Standard 1037C, definition: general purpose computer, Mar. 6, 2013, Institute for Telecommunication Sciences.*
The Electrical Journal, vol. XV Jan.-Dec. 1918, pp. 124-128 (Year: 1918).*

* cited by examiner

VIBRATION SENSOR ASSEMBLY FOR PROGNOSTIC AND DIAGNOSTIC HEALTH ASSESSMENT OF A POWER CIRCUIT BREAKER'S POWER TRANSMISSION AND DISTRIBUTION SYSTEM IN REAL TIME

BACKGROUND OF THE INVENTION

Field of the Invention

The disclosed and claimed concept relates to a circuit breaker and switchgear assembly with a component monitoring system and, more specifically, to circuit breaker assembly with a modular component monitoring system including a vibration sensor assembly.

Background Information

Circuit breaker assemblies provide protection for electrical systems from electrical fault conditions such as current overloads, short circuits, and low level voltage conditions. Typically, circuit breakers include a trip device and an operating mechanism. The trip device detects an over-current condition and actuates the operating mechanism. The operating mechanism open and closes, either manually or in response to the trip device, a number of electrical contacts. These trip devices and protective relays are housed inside a switchgear cell along with the circuit breakers. In an exemplary embodiment, the operating mechanism utilizes a number of springs to generate force for the opening and closing operations. Further, the springs are maintained in a charged state so that, for example, following an over-current condition, the contacts may be closed without having to charge the springs.

The components of a circuit breaker assembly, such as, but not limited to, the operating mechanism components are subject to wear and tear over time. The signal output of other ancillary devices, such as, but not limited to, protective relays, trip units, etc., are also affected due to wear and tear of operating mechanisms and other subassemblies of the circuit breaker. When an operating mechanism component becomes worn, the operating mechanism component should be replaced before it fails during its service, which would cause power outage and increased unscheduled downtime. Rather than waiting for an operating mechanism component to become worn to the point of needing replacement, it is desirable to replace the operating mechanism component preemptively. The focus of the maintenance schedule has already been changed from planned to preventive maintenance. However, further advancement is needed to change it further to Reliability Centered Maintenance (RCM) where the component failure with its failure mode is predicted in priori and a maintenance is arranged at appropriate time in advance. That is, it is desirable to continuously monitor the "health" of the circuit breaker and switchgear subassemblies, operating mechanism components and diagnose when an operating mechanism component will need replaced.

There is, therefore, a need for a component monitoring system and predictive methodology that are structured to monitor circuit breaker assembly operating mechanism component characteristics, as well as other components such as, but not limited to, switchgear, power distribution and transmission system components. Further, there is a need for a modular, portable, 'plug and play' type and retrofitable component monitoring system that may be moved between circuit breakers.

SUMMARY OF THE INVENTION

These needs, and others, are met by at least one embodiment of the disclosed and claimed embodiments which provides for a component monitoring system structured to monitor circuit breaker assembly sub-assemblies and their component's characteristics. Hereinafter, the specification will use operating mechanism components as an example. It is understood, however, that the component monitoring system is structured to monitor any circuit breaker assembly sub-assemblies and their component's characteristics and is not limited to monitoring operating mechanism components. The component monitoring system includes a record assembly, a number of sensor assemblies, a comparison assembly, and an output assembly. The record assembly includes selected nominal data for a selected circuit breaker component, a number of circuit breaker components, substantially all of the circuit breaker assembly, or all of the circuit breaker assembly. The sensor assembly is structured to measure a number of actual component characteristics of a selected circuit breaker component, a number of circuit breaker components, substantially all of the circuit breaker assembly, or all of the circuit breaker assembly, and to transmit actual component characteristic output data. The comparison assembly is structured to receive an electronic signal from said record assembly and said sensor assemblies, to compare said sensor assembly actual component characteristic output data to said selected nominal data or the failure predictive algorithm that analyzes the raw sensor data with some form of statistical methodology (such as, but not limited to parallel format) or serial monitoring format, and to provide an indication signal as to whether said sensor assembly output data is acceptable when compared to the selected nominal data. The output assembly includes a communication assembly and an output device. The communication assembly is structured to receive an indication signal from the comparison assembly and to communicate a signal to said output device. Each sensor assembly is in electronic communication with the comparison assembly. The comparison assembly is in electronic communication with the communication assembly. In an exemplary embodiment, the number of sensor assemblies includes a number of vibration sensor assemblies, such as, but not limited to accelerometers. The number of sensor assemblies are structured to measure actual component characteristics, i.e. vibrations, in substantially all of the circuit breaker assembly.

BRIEF DESCRIPTION OF THE DRAWINGS

A full understanding of the invention can be gained from the following description of the preferred embodiments when read in conjunction with the accompanying drawings in which:

FIG. 10 is a top view of a monitoring latch assembly.

DESCRIPTION OF THE PREFERRED EMBODIMENTS

Figure 1:
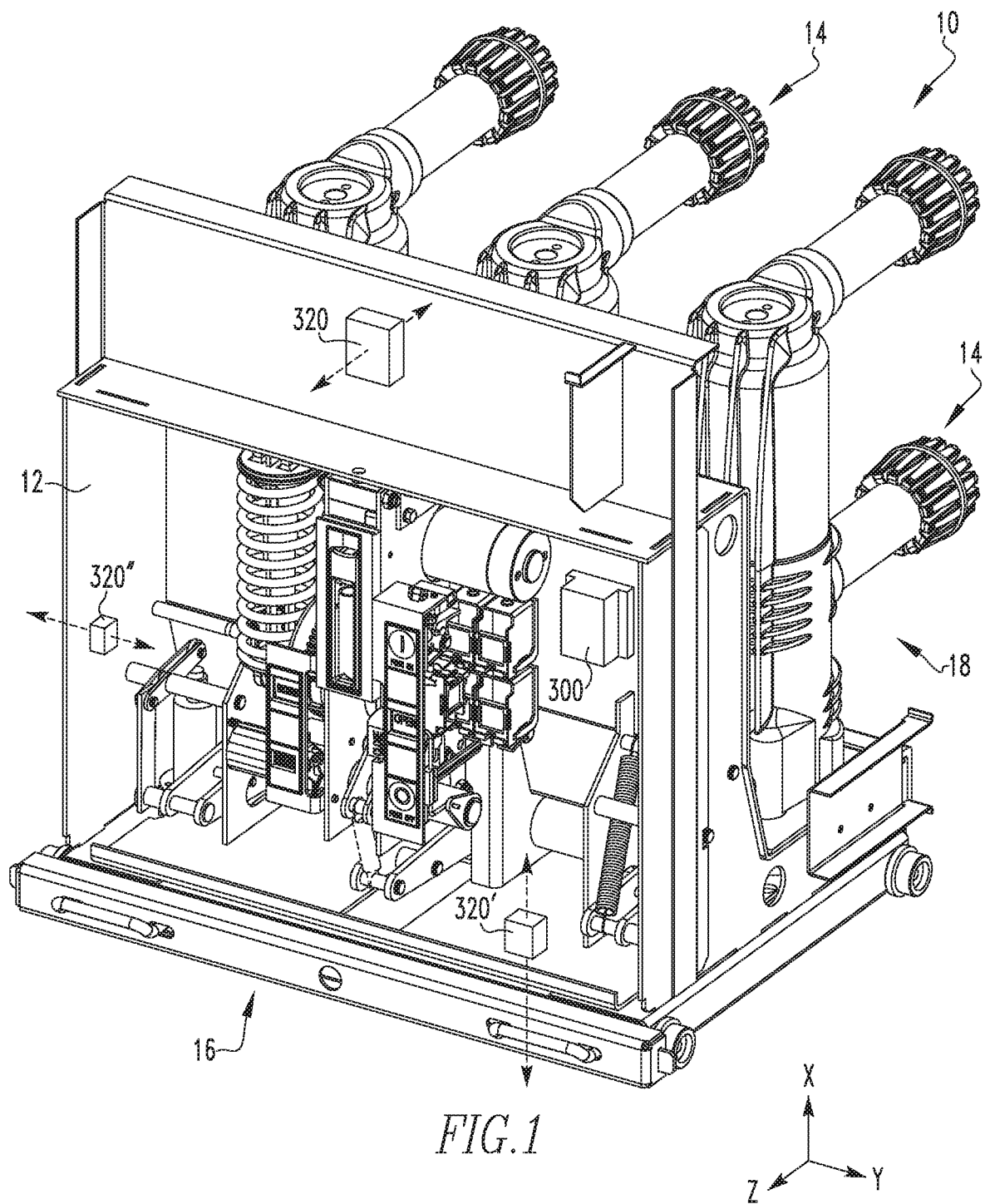
FIG. 1 is an isometric view of a circuit breaker assembly.

It will be appreciated that the specific elements illustrated in the figures herein and described in the following specification are simply exemplary embodiments of the disclosed concept, which are provided as non-limiting examples solely for the purpose of illustration. Therefore, specific dimensions, orientations, assembly, number of components used, embodiment configurations and other physical characteristics related to the embodiments disclosed herein are not to be considered limiting on the scope of the disclosed concept.

Directional phrases used herein, such as, for example, clockwise, counterclockwise, left, right, top, bottom, upwards, downwards and derivatives thereof, relate to the orientation of the elements shown in the drawings and are not limiting upon the claims unless expressly recited therein.

As used herein, the singular form of "a," "an," and "the" include plural references unless the context clearly dictates otherwise.

As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. It is noted that moving parts, such as but not limited to circuit breaker contacts, are "directly coupled" when in one position, e.g., the closed, second position, but are not "directly coupled" when in the open, first position. As used herein, "fixedly coupled" or "fixed" means that two components are coupled so as to move as one while maintaining a constant orientation relative to each other. Accordingly, when two elements are coupled, all portions of those elements are coupled. A description, however, of a specific portion of a first element being coupled to a second element, e.g., an axle first end being coupled to a first wheel, means that the specific portion of the first element is disposed closer to the second element than the other portions thereof.

As used herein, the phrase "removably coupled" means that one component is coupled with another component in an essentially temporary manner. That is, the two components are coupled in such a way that the joining or separation of the components is easy and would not damage the components. For example, two components secured to each other with a limited number of readily accessible fasteners are "removably coupled" whereas two components that are welded together or joined by difficult to access fasteners are not "removably coupled." A "difficult to access fastener" is one that requires the removal of one or more other components prior to accessing the fastener wherein the "other component" is not an access device such as, but not limited to, a door.

As used herein, "operatively coupled" means that a number of elements or assemblies, each of which is movable between a first position and a second position, or a first configuration and a second configuration, are coupled so that as the first element moves from one position/configuration to the other, the second element moves between positions/configurations as well. It is noted that a first element may be "operatively coupled" to another without the opposite being true.

As used herein, "characteristics" of elements or assemblies include, but are not limited to, the position of the elements or assemblies, distance moved by one or more of the elements or assemblies, the force generated within or between one or more of the elements or assemblies, or stress within one or more of the elements or assemblies. The measurable characteristic motion may be linear, angular (in 2D or 3D references) and may be convertible to another type of motion with appropriate calibration (factory or field set). The characteristic can be converted into another form (such as, but not limited to, electrical energy, electromechanical energy/force, magnetic, thermal, etc.).

As used herein, a "coupling assembly" includes two or more couplings or coupling components. The components of a coupling or coupling assembly are generally not part of the same element or other component. As such, the components of a "coupling assembly" may not be described at the same time in the following description.

As used herein, a "coupling" or "coupling component(s)" is one or more component(s) of a coupling assembly. That is, a coupling assembly includes at least two components that are structured to be coupled together. It is understood that the components of a coupling assembly are compatible with each other. For example, in a coupling assembly, if one coupling component is a snap socket, the other coupling component is a snap plug, or, if one coupling component is a bolt, then the other coupling component is a nut.

As used herein, a "fastener" is a separate component structured to couple two or more elements. Thus, for example, a bolt is a "fastener" but a tongue-and-groove coupling is not a "fastener." That is, the tongue-and-groove elements are part of the elements being coupled and are not a separate component.

As used herein, "correspond" indicates that two structural components are sized and shaped to be similar to each other and may be coupled with a minimum amount of friction. Thus, an opening which "corresponds" to a member is sized slightly larger than the member so that the member may pass through the opening with a minimum amount of friction. This definition is modified if the two components are to fit "snugly" together. In that situation, the difference between the size of the components is even smaller whereby the amount of friction increases. If the element defining the opening and/or the component inserted into the opening are made from a deformable or compressible material, the opening may even be slightly smaller than the component being inserted into the opening. With regard to surfaces, shapes, and lines, two, or more, "corresponding" surfaces, shapes, or lines have generally the same size, shape, and contours.

As used herein, a "computer" is a device structured to process data having at least one input device, e.g. a keyboard, mouse, or touch-screen, at least one output device, e.g. a display, a graphics card, a communication device, e.g. an Ethernet card or wireless communication device, permanent memory, e.g. a hard drive, temporary memory, i.e. random access memory, and a processor, e.g. a programmable logic circuit. The "computer" may be a traditional desktop unit but also includes cellular telephones, tablet computers, laptop computers, as well as other devices, such as gaming devices that have been adapted to include components such as, but not limited to, those identified above. Further, the "computer" may include components that are physically in different locations. For example, a desktop unit may utilize a remote hard drive for storage. Such physically separate elements are, as used herein, a "computer."

As used herein, the word "display" means a device structured to present a visible image. Further, as used herein, "present" means to create an image on a display which may be seen by a user.

As used herein, a "computer readable medium" includes, but is not limited to, hard drives, CDs, DVDs, magnetic tape, floppy drives, and random access memory.

As used herein, "permanent memory" means a computer readable storage medium and, more specifically, a computer readable storage medium structured to record information in a non-transitory manner. Thus, "permanent memory" is limited to non-transitory tangible media.

As used herein, "stored in the permanent memory" means that a module of executable code, or other data, has become functionally and structurally integrated into the storage medium.

As used herein, a "file" is an electronic storage construct for containing executable code that is processed, or, data that may be expressed as text, images, audio, video or any combination thereof.

As used herein, a "module" is an electronic construct used by a computer, or other processing assembly, and includes, but is not limited to, a computer file or a group of interacting computer files such as an executable code file and data storage files, used by a processor and stored on a computer readable medium. Modules may also include a number of other modules. It is understood that modules may be identified by their purpose of function. Unless noted otherwise, each "module" is stored in permanent memory of at least one computer or processing assembly. All modules are shown schematically in the Figures.

As used herein, and in the phrase "[x] moves between a first position and a second position corresponding to [y] first and second positions," wherein "[x]" and "[y]" are elements or assemblies, the word "correspond" means that when element [x] is in the first position, element [y] is in the first position, and, when element [x] is in the second position, element [y] is in the second position. It is noted that "correspond" relates to the final positions and does not mean the elements must move at the same rate or simultaneously. That is, for example, a hubcap and the wheel to which it is attached rotate in a corresponding manner. Conversely, a spring biased latched member and a latch release move at different rates. That is, as an example, a latch release moves between a first position, wherein the latched member is not released, and a second position, wherein the latched member is released. The spring-biased latched member moves between a first latched position and a second released position. The latch release may move slowly between positions and, until the release is in the second position, the latched member remains in the first position. But, as soon as the latch release reaches the second position, the latched member is released and quickly moves to the second position. Thus, as stated above, "corresponding" positions mean that the elements are in the identified first positions at the same time, and, in the identified second positions at the same time.

As used herein, the statement that two or more parts or components "engage" one another shall mean that the elements exert a force or bias against one another either directly or through one or more intermediate elements or components. Further, as used herein with regard to moving parts, a moving part may "engage" another element during the motion from one position to another and/or may "engage" another element once in the described position. Thus, it is understood that the statements, "when element A moves to element A first position, element A engages element B," and "when element A is in element A first position, element A engages element B" are equivalent statements and mean that element A either engages element B while moving to element A first position and/or element A either engages element B while in element A first position.

As used herein, "operatively engage" means "engage and move." That is, "operatively engage" when used in relation to a first component that is structured to move a movable or rotatable second component means that the first component applies a force sufficient to cause the second component to move. For example, a screwdriver may be placed into contact with a screw. When no force is applied to the screwdriver, the screwdriver is merely "coupled" to the screw. If an axial force is applied to the screwdriver, the screwdriver is pressed against the screw and "engages" the screw. However, when a rotational force is applied to the screwdriver, the screwdriver "operatively engages" the screw and causes the screw to rotate.

As used herein, the word "unitary" means a component that is created as a single piece or unit. That is, a component that includes pieces that are created separately and then coupled together as a unit is not a "unitary" component or body.

As used herein, the term "number" shall mean one or an integer greater than one (i.e., a plurality).

As used herein, "associated" means that the elements are part of the same assembly and/or operate together, or, act upon/with each other in some manner. For example, an automobile has four tires and four hub caps. While all the elements are coupled as part of the automobile, it is understood that each hubcap is "associated" with a specific tire.

As used herein, in the phrase "[x] moves between its first position and second position," or, "[y] is structured to move [x] between its first position and second position," "[x]" is the name of an element or assembly. Further, when [x] is an element or assembly that moves between a number of positions, the pronoun "its" means "[x]," i.e. the named element or assembly that precedes the pronoun "its."

As used herein, "in electronic communication" is used in reference to communicating a signal via an electromagnetic wave or signal. "In electronic communication" includes both hardline and wireless forms of communication; thus, for example, a "data transfer" or "communication method" via a component "in electronic communication" with another component means that data is transferred from one computer to another computer (or from one processing assembly to another processing assembly) by physical connections such as USB, Ethernet connections or remotely such as NFC, blue tooth etc. and should not be limited to any specific device.

As used herein, "in electric communication" means that a current passes, or can pass, between the identified elements. Being "in electric communication" is further dependent upon an element's position or configuration. For example, in a circuit breaker, a movable contact is "in electric communication" with the fixed contact when the contacts are in a closed position. The same movable contact is not "in electric communication" with the fixed contact when the contacts are in the open position.

Figure 2:
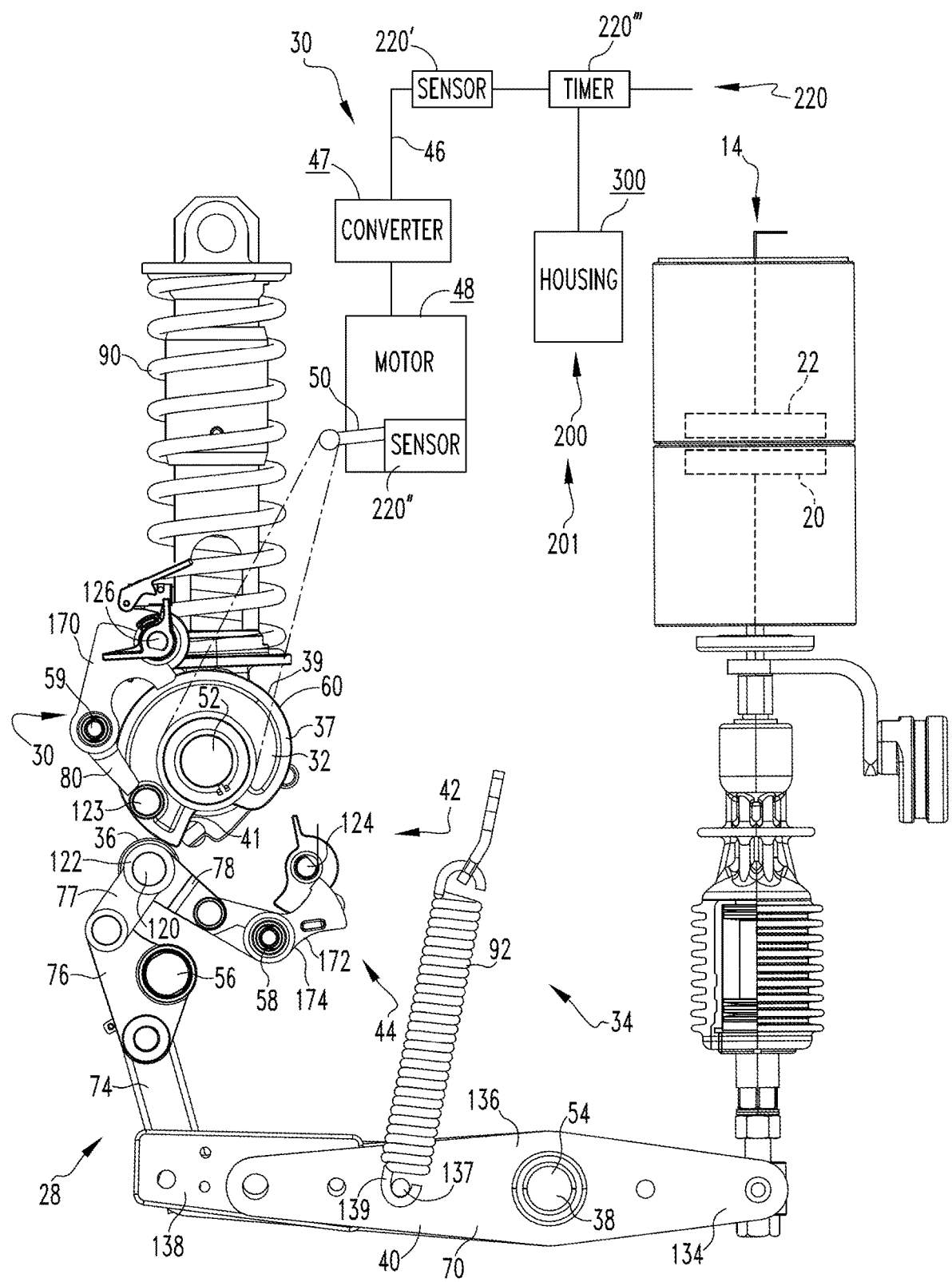
FIG. 2 is a side view of a circuit breaker assembly.

A circuit breaker assembly 10 is shown, in part schematically, in FIGS. 1 and 2. The circuit breaker assembly 10 includes a housing assembly 12, a conductor assembly 14, an operating mechanism 16, and a trip assembly 18 (some elements shown schematically). The conductor assembly 14 includes a number of conductive members, discussed below, which are in electrical communication with a line and a load, not shown. In an exemplary embodiment, any "conductive" element is made from a conductive metal such as, but not limited to, copper, aluminum, gold, silver, or platinum. The conductor assembly 14 includes a movable contact assembly 20 and a fixed contact assembly 22. The operating mechanism 16 is operatively coupled to the movable contact assembly 20 and is structured to move the movable contact assembly 20 between an open, first position, wherein the movable contact assembly 20 is effectively spaced from the fixed contact assembly 22, and a closed, second position, wherein the movable contact assembly 20 is coupled to, and in electrical communication with, the fixed contact assembly 22.

The operating mechanism 16 includes a number of components 28 each of which has a number of characteristics. In an exemplary embodiment, the operating mechanism components 28 include, but are not limited to, a charging motor assembly 30, number of cam members 32, a number of springs 34, a number of cam followers 36, a number of shafts 38, a number of link members 40, a number of D-shafts 42, and a number of latch members 44. It is understood that FIG. 2 is a schematic view showing a limited number of operating mechanism components 28. For example, as is known and in an exemplary embodiment, a circuit breaker assembly 10 includes a number of poles, such as but not limited to three poles. Further, there is a movable contact assembly 20 and a fixed contact assembly 22 associated with each pole. Further, it is understood that each movable contact assembly 20 is coupled to a contact spring 94 (Shown schematically), discussed below. It is understood that the contact spring 94 may be disposed within a housing assembly disposed about the movable contact assembly 20. Generally, the operating mechanism 16 moves through a number of configurations, e.g. open, close, trip (contact assembly 20 open and closing spring discharged and thereafter charged), and reset, however, for the purpose of this disclosure the operating mechanism 16 shall be identified as being in either an open, first configuration, or a closed, second configuration; the operating mechanism 16 configurations correspond to the position of the movable contact assembly 20. That is, when the movable contact assembly 20 is in the first position, the operating mechanism 16 is in the first configuration, and, when the movable contact assembly 20 is in the second position, the operating mechanism 16 is in the second configuration.

In an exemplary embodiment, the operating mechanism components 28 are operatively coupled together. Further, the operating mechanism components 28 are operatively coupled to the trip assembly 18. In this configuration, the operating mechanism 16 is structured to move the movable contact assembly 20 between the first position and second position, as noted above. Further, the operating mechanism 16 is structured to move the movable contact assembly 20 from the second position to the first position in response to an overcurrent condition detected by the trip assembly 18. In an exemplary embodiment, the number of springs 34 are structured to cause a rapid movement of the movable contact assembly 20 between positions. That is, generally, a spring 34 is compressed prior to moving the movable contact assembly 20 and, when the movable contact assembly 20 is to be moved, the spring 34 is released causing a rapid movement of the movable contact assembly 20.

The charging motor assembly 30, shown schematically, is, in an exemplary embodiment, an electric motor. The charging motor assembly 30 is coupled to the housing assembly 12. The charging motor assembly 30 includes a rotating output shaft 50. In an exemplary embodiment, the charging motor assembly 30 includes an AC conductor 46, an AC/DC converter 47, and a DC motor 48. The output shaft 50 is, in an exemplary embodiment, part of the DC motor 48. The AC conductor 46 is coupled to, and in electrical communication with, an AC line (not shown) as well as the AC/DC converter 47. The AC/DC converter 47 is coupled to, and in electrical communication with, the DC motor 48. In this configuration, current passes through the AC conductor 46 and the AC/DC converter 47 during the actuation of the DC motor 48.

The number of shafts 38 includes a cam drive shaft 52 a rocker link shaft 54, a lay shaft 56, a close latch shaft 58 and a trip latch shaft 59. It is understood, and shown schematically, that each shaft 38 is either rotatably coupled to the housing assembly 12 or fixed to the housing assembly 12 (shown in FIG. 1). Thus, it is understood that a rotating shaft 38 rotates about a longitudinal axis of rotation. Conversely, components 28 may rotate about a fixed shaft 38. The charging motor assembly output shaft 50 is operatively coupled to the cam drive shaft 52. As such, actuation of the charging motor assembly 30 causes the cam drive shaft 52 to rotate. As described below, the rocker link shaft 54 is coupled, directly coupled or fixed to a number of rocker link members 70.

The number of cam members 32 includes a first charging cam 60. The first charging cam 60 is coupled, directly coupled or fixed to the cam drive shaft 52 in a fixed orientation. Thus, the first charging cam 60 and the cam drive shaft 52 rotate with each other. That is, actuation of the charging motor assembly 30 causes the first charging cam 60 to rotate. Further, various spring 34 forces, acting through various link members 40, cause the first charging cam 60, and therefore the cam drive shaft 52, to rotate. Rotation of the cam drive shaft 52 does not cause the charging motor assembly output shaft 50 to rotate.

The number of link members 40 includes, but is not limited to, a rocker link member 70, a first link member 74, a lay shaft casting link member 76, a main link coupler member 77, a main link member 78, and a close latch link member 80. Generally, each link member 40 includes an elongated body with a first end and a second end, which will be identified by reference numbers as needed below. A rotational coupling, which will be identified by reference numbers as needed below, is disposed at each link end. A rotational coupling may be any coupling that allows rotation such as, but not limited to an opening in each link end with a pin through both link end openings.

The number of springs 34 includes a closing spring 90, an opening spring 92, and a contact spring 94. Generally, each spring 34 includes a body with a first end and a second end, which will be identified by reference numbers as needed below. In an exemplary embodiment, each spring 34 is a compression spring. As noted above, the schematic side view of FIGS. 2, 2A shows a single closing spring 90, opening spring 92, and contact spring 94; it is understood that there may be, and typically are, a number of each named spring 90, 92, 94. Each closing spring 90 is charged, i.e. compressed, prior to moving the movable contact assembly 20 from the first position to the second position. That is, each closing spring 90 is charged and the energy is released to rapidly move the movable contact assembly 20 from the first position to the second position. Each opening spring 92 is charged, i.e. compressed, prior to moving the movable contact assembly 20 from the second position to the first position. That is, each opening spring 92 is charged and the energy is released to rapidly move the movable contact assembly 20 from the second position to the first position. The closing springs 90 and the opening springs 92 may be charged at any time prior to the associated movement of the movable contact assembly 20. That is, for example, the opening springs 92 are charged as soon as the movable contact assembly 20 moves to the second position and are maintained in the charged state in the event of an overcurrent condition at a later time. Similarly, the closing springs 90 are charged as soon as the movable contact assembly 20 moves to the second position so that, following an overcurrent condition and subsequent opening of the contact assemblies 20, 22, the movable contact assembly 20 can be returned to the second position. The contact spring 94 is structured to bias the movable contact assembly 20 toward the fixed contact assembly 22 when the movable contact assembly 20 is in the second position. Thus, during normal operation, i.e. when the movable contact assembly 20 is in the closed, second position and in an exemplary embodiment, the closing spring 90, the opening spring 92, and the contact spring 94 are each charged. Thus, the spring forces, also identified as reactive spring forces, act upon any other operating mechanism components 28 that are operatively coupled to the springs 34.

The number of cam followers 36 includes a closing spring cam follower 120 and a main roller 122. It is understood that a cam follower 36 operatively engages a cam member 32, is operatively engaged by a cam member 32, or both. A cam follower 36, in an exemplary embodiment, is a wheel-like roller structured to engage the outer surface of a cam member 32. That is, in an exemplary embodiment, a cam member 32 is a generally planar, disk-like body 37 including a spiral radial surface 39 with an offset 41, i.e. a generally radial step. A cam follower 36 travels over, and engages the cam member body radial surface 39. Thus, because the cam member body radial surface 39 is not a constant distance from the center of the cam member body 37, which is the axis of rotation, the cam follower 36 moves closer or further from the center of the cam member body 37.

The number of D-shafts 42 includes a trip latch D-shaft 124 and a close latch D-shaft 126. Each D-shaft 42 is rotatably coupled to the housing assembly 12. Each D-shaft 42 operatively engages, and/or is operatively engaged by, a latch member 44. The latch members 44 are discussed in detail below. Generally, however, a latch member 44 is movable and includes a latching surface, discussed below, that is disposed adjacent to a D-shaft 42. When the D-shaft is in a first orientation, the curved portion of the D-shaft surface is disposed in the path of travel of the latch member latching surface. When the D-shaft 42 rotates to a second orientation, wherein the flat portion of the D-shaft surface is disposed adjacent the latch member 44, the D-shaft surface is not disposed in the path of travel of the latch member engagement surface. Thus, in one orientation, the D-shaft 42 blocks the travel of the latch member 44. This is the latched orientation of the D-shaft 42 wherein the associated latch member 44 is latched. In the other orientation, the D-shaft 42 does not block the travel of the latch member 44. This is the unlatched orientation of the D-shaft 42 wherein the associated latch member 44 is unlatched.

In an exemplary embodiment, the identified operating mechanism components 28 are assembled as follows. A contact spring first end 130, shown schematically, is coupled, directly coupled, or fixed to the movable contact assembly 20. A contact spring second end 132 is coupled, directly coupled, or rotatably coupled to a rocker link member first end 134. A rocker link member medial portion 136 is coupled, directly coupled, or fixed to rocker link shaft 54. Further, the rocker link member 70 includes an opening spring mounting 137 disposed between the rocker link member medial portion 136 and a rocker link member second end 138. An opening spring first end 139 is coupled, directly coupled, or fixed to the rocker link member opening spring mounting 137.

In an exemplary embodiment, the rocker link shaft 54 is rotatably coupled to the housing assembly 12 and the rocker link member 70 is fixed to the rocker link shaft 54. The rocker link member second end 138 is coupled, directly coupled, or rotatably coupled to a first link first end 140. A first link second end 142 is coupled, directly coupled, or rotatably coupled to a lay shaft casting link member first end 144. An offset lay shaft casting link member medial portion 146 is rotatably coupled to the lay shaft 56. The lay shaft 56 is coupled, directly coupled, or fixed to the housing assembly 12. A lay shaft casting link member second end 148 is coupled, directly coupled, or rotatably coupled to a main link coupler member first end 150. A main link coupler member second end 152 is coupled, directly coupled, or rotatably coupled to a main link member first end 154. Further, the main roller 122 is rotatably coupled to a rotational coupling at the interface of the main link coupler member second end 152 and the main link member first end 154. A main link member second end 156 is coupled, directly coupled, or rotatably coupled to a trip latch member body latching first end 184 (FIG. 9), discussed below.

Further, the first charging cam 60 is fixed to the cam drive shaft 52, as described above. The first charging cam 60 is disposed adjacent to the main roller 122. That is, the first charging cam 60 is disposed so that the main roller 122 operatively engages the first charging cam member body radial surface 39. A close latch member 170, discussed below, is disposed adjacent to the first charging cam 60. In an exemplary embodiment, the close latch member 170 is rotatably coupled to the close latch shaft 58. The close latch shaft 58 is coupled, directly coupled, or fixed to the housing assembly 12. A close latch link member first end 160 is coupled, directly coupled, or rotatably coupled to a close latch member first end 171, discussed below. A close latch link member second end 162 is rotatably coupled to the close latch follower 123.

The configuration described above is an exemplary embodiment of an operating mechanism 16 that is structured to move the movable contact assembly 20 between an open, first position, wherein the movable contact assembly 20 is effectively spaced from the fixed contact assembly 22, and a closed, second position, wherein the movable contact assembly 20 is coupled to, and in electrical communication with, the fixed contact assembly 22. Movement of the movable contact assembly 20 may be intentionally initiated or be in response to an overcurrent condition, i.e. initiated by the trip assembly 18.

The circuit breaker assembly 10, and in an exemplary embodiment the operating mechanism 16, includes a component monitoring system 200 structured to monitor a number of circuit breaker assembly components' characteristics including those of operating mechanism 16 as exemplified above. In an exemplary embodiment, the component monitoring system 200 is a displaced component monitoring system 201. As used herein, a "displaced component monitoring system" 201 means a system wherein a first component is monitored so as to diagnose a characteristic of a different, second component. Three exemplary embodiments of the component monitoring system 200, which are also displaced component monitoring systems 201, are discussed below. Generally, a component monitoring system 200 is structured to measure a component characteristic, such as, but not limited to, the force generated by a charged spring 34 while in the second configuration. Further, the component monitoring system 200 compares the measured component characteristic to a selected nominal component characteristic. The "selected nominal" component characteristic data, alternatively "selected nominal data," as used herein, are determined via use, testing or determined theoretically and is utilized as a standard template against which the acquired data is compared. The "selected nominal data" may be defined specifically, as a range, or as a coefficient.

For example, each mechanism motion and its characteristics are governed by selected mathematical equations associated with the specific physical form of the components. These equations may be linear or nonlinear, partial or ordinary derivative in nature. The equations correlate the dependent variables (such as but not limited to, contact wear, contact moving speed, forces, and displacements etc.) and some independent variables (such as, but not limited to, linkages ratio, linkage length, spring characteristics e.g. length, spring constant etc.). Such equations may take a generalized form, such as, but not limited to.

$$y_1 = \beta_1 f_1(t_1) + \beta_2 f_2(t_2) + \beta_3 f_3(t_3) + \ldots + \beta_k f_k(t_k) + \ldots + \varepsilon.$$

Or, $$y_1 = \beta_1 f_1(t_1, t_2, t_3, \ldots t_n) + \beta_2 f_2(t_1, t_2, t_3, \ldots t_n) + \ldots + \varepsilon.$$

Or, $$y_1 = \beta_1 f'_1(t_1, t_2, t_3, \ldots t_n) + \beta_2 f'_2(t_1, t_2, t_3, \ldots t_n) + \ldots + \varepsilon.$$

The multipliers ($\beta_n$), associated with directly or indirectly independent variables ($f_n(t_n)$ or $f_n(t_1, t_2, t_3, \ldots t_n)$ or $f_n'(t_1, t_2, t_3, \ldots t_n)$) are, as used herein, "coefficients." A detailed example is provided below. The right side of the equation can be identified as the "physics of operation" of the system whereas the left side of the equation can be identified as a "physically expected dependent variable." The difference between the left side of the equation and right side of the equation are due to experimental errors or unknown factors in practice etc., can be associated to a or the error term.

Further, as used herein "selected nominal data" may be associated with any component characteristic. Alternatively, a specific component characteristic, and nominal data associated therewith, may be identified by a specific name. For example if the relevant component characteristic is the "correlation coefficient" (discussed below), then the "selected nominal data" for that component characteristic is identified as "selected nominal correlation coefficient" data. Further, data acquired or collected during use of a circuit breaker assembly 10 is, as used herein, "acquired selected nominal data." Further, data acquired or collected during use of the circuit breaker assembly 10 to which the component monitoring system 200 is coupled to is, as used herein, "acquired local selected nominal data."

Figure 3:
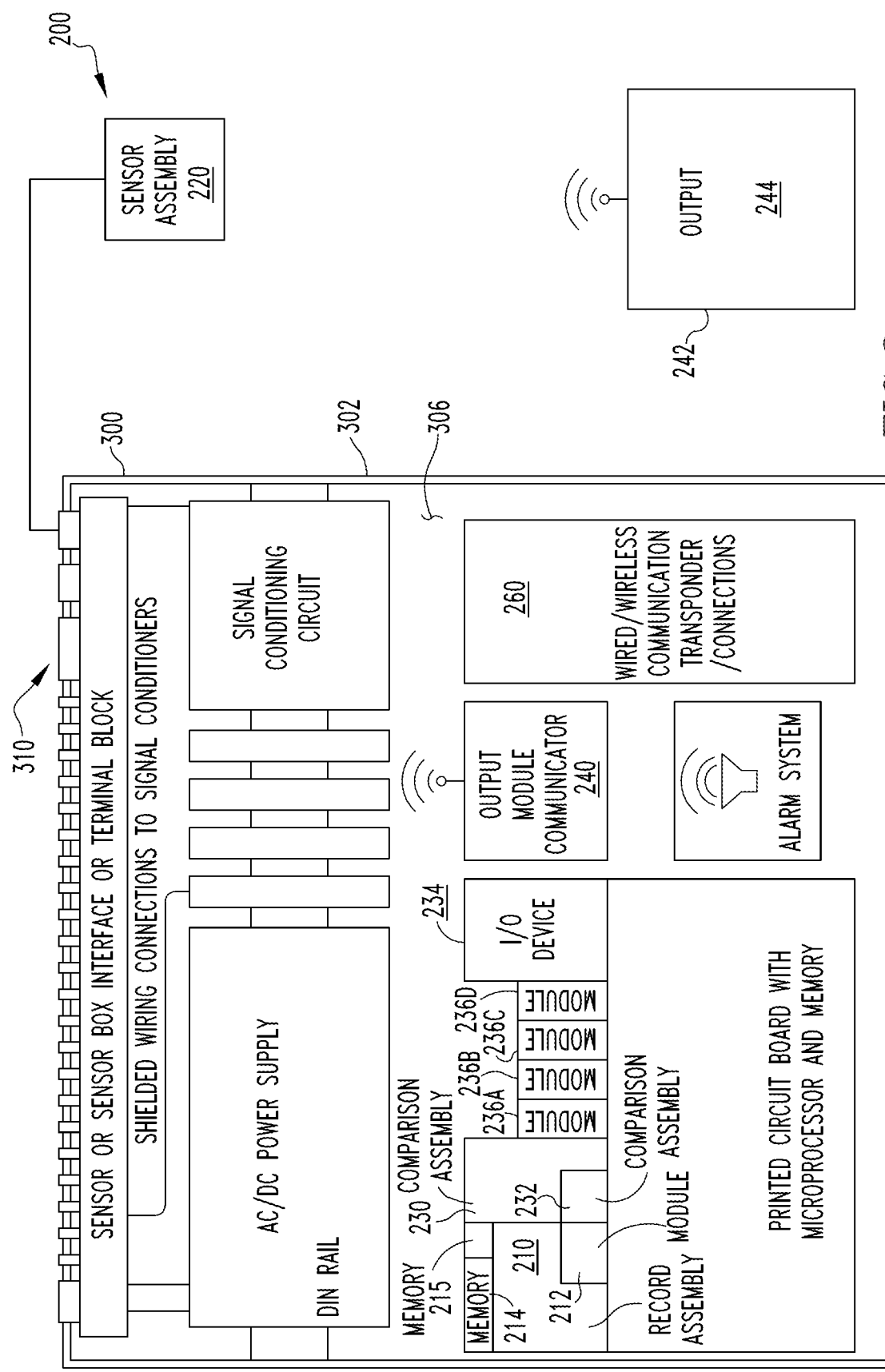
FIG. 3 is a schematic view of a component monitoring system.

As shown in FIG. 3, the component monitoring system 200 includes a record assembly 210, at least one sensor assembly 220, or a number of sensor assemblies 220, a comparison assembly 230, and an output assembly 240. The record assembly 210 is, in an exemplary embodiment, a database module 212 stored in a memory assembly 214 and/or permanent memory assembly 215. As used herein, the memory assembly 214 and/or permanent memory assembly 215 include any electrical memory device such as, but not limited to, a magnetic drive, flash memory, or an optical drive, but does exclude transitory media. The record assembly 210, and in an exemplary embodiment the database module 212, includes data representing selected nominal data of a number of selected operating mechanism components 28.

Further, the database module 212 is structured to be updated. That is, the selected nominal data may be replaced or amended, e.g., additional data may be added to the selected nominal data. Updating the selected nominal data, in an exemplary embodiment, occurs following a failure of an operating mechanism component 28.

For example, it is understood that as the condition of closing spring 90 deteriorates, the closing spring 90 becomes more stiff causing a change in the spring constant of the closing spring 90. Thus, the selected nominal data, in an exemplary embodiment, includes data representing a minimum closing time for the closing spring 90 as well as a range indicating the acceptable stress on closing spring 90 when the movable contact assembly 20 is in the second position. Upon failure of the closing spring 90, e.g. a failure to close within the minimum closing time, the last recorded stress on the closing spring 90 is added to the selected nominal data associated with the closing spring 90. Such new data is "acquired local selected nominal data," as discussed above. Such acquired local selected nominal data is subsequently used by the comparison assembly 230, as discussed below. Alternatively, the new data may be copied to other component monitoring systems 200 in other circuit breaker assemblies; in this instance, the data is "acquired selected nominal data." It is understood that by updating the selected nominal data the component monitoring system 200 improves its predictions of remaining useful life (RUL), as discussed below. Stated alternately, the component monitoring system 200 learns new operating mechanism component 28 characteristics that indicate failure.

Further, in an exemplary embodiment, the selected nominal data is stored in a "reduced data set." As used herein, a "reduced data set" means that the amount of data stored is limited to a set of between two and five numbers, i.e. 20-40 bytes per sensor assembly 220. For example, if the selected nominal data is "coefficient data," then the coefficients can be stored directly or indirectly by associating them with some form of statistical distribution function e.g.

$$\beta_n \sim N(\beta_n^{average}, \beta_n^{variance}) \text{ or } \beta_n \sim W(\beta_n^{scale}, \beta_n^{shape}),$$

where, N represents normal distribution and W represents Weibull distribution functions and the stored parameters would be either $\beta_n$ and/or ($\beta_n^{average}$, $\beta_n^{variance}$).

The record assembly 210 is, in an exemplary embodiment, also in electronic communication with the output assembly 240. For example, if the output assembly 240 includes a display 244, the record assembly 210 is in electronic communication with the display 244 and is structured to present data on the display 244. As discussed below, the comparison assembly 230 is also in electronic communication with the display 244 and is structured to present actual component characteristics. Thus, a user, in an exemplary embodiment, can visually compare the actual component characteristics to the selected nominal data. For example, the selected nominal data may be in the form of an acceptable range. This range may be presented on the display 244. The actual component characteristic may be presented as a data point relative to that range. Thus, a user can see if the actual component characteristic is within the acceptable range or not, and how close the actual component characteristic is to being outside the acceptable range. In another exemplary embodiment, not shown, the selected nominal data is printed on a transparent film and is mounted on a display 244. The selected nominal data may be presented or shown in other manners as well.

In an exemplary embodiment, each sensor assembly 220 includes, or is structured to be coupled to and in electronic communication with, a power source (not shown). The power source may be disposed within each sensor assembly 220. Further, each sensor assembly 220 is structured to measure a number of "actual component characteristics," as defined below, of a sub-assembly of the circuit breaker assembly 10, such as, but not limited to a selected operating mechanism component 28. Alternatively, a sensor assembly 220 is structured to measure a number of actual component characteristics of a number of circuit breaker assembly sub-assemblies, a substantial portion of the circuit breaker assembly 10, or, the entire circuit breaker assembly 10, as discussed below. The component characteristics that are physically measured, such as, but not limited to, deformation of the sub-assembly of the circuit breaker assembly 10, such as, but not limited to a selected operating mechanism component 28 are the "measured component characteristics" as used herein. Further, a sub-assembly of the circuit breaker assembly 10, such as, but not limited to a selected operating mechanism component 28 may be associated with more than one sensor assembly 220. Generally hereinafter, however, as an initial example and for simplicity, it is assumed that there is a single sensor assembly 220 structured to measure a single actual component characteristic. The sensor assembly 220 is further structured to transmit output data representing the selected circuit breaker component's actual component characteristic. In this exemplary embodiment, the output data is an electronic construct such as, but not limited to, a signal. Hereinafter, the "output data representing the selected circuit breaker component's actual component characteristic" is identified as "actual component characteristic output data." In an exemplary embodiment, the actual component characteristic output data signal has characteristics of between about 0-10V DC, between about 4-20 mA and between about 100-1000 Hz, or, digital signal output. As stated, this is an example and is not limiting.

The comparison assembly 230 includes a processing assembly 232, an input/output device 234, and a comparison module 236. The processing assembly 232 includes a programmable logic circuit, memory, and an infrastructure, such as, but not limited to a printed circuit board (none shown). As used herein, a "processing assembly" is not a general purpose computer. The processing assembly 232 is structured to execute the comparison module 236. The comparison module 236, when executed, is structured to acquire the selected nominal data for the selected component from the record assembly 210 and to record "actual component characteristics." That is, as used herein, "actual component characteristics" means the measured component characteristics (in an exemplary embodiment, represented by the actual component characteristic output data) and/or "calculated component characteristics." "Calculated component characteristics" means component characteristics based on measured component characteristics and equations such as, but not limited to, the equations set forth below.

In an exemplary embodiment, the comparison assembly 230, and in an exemplary embodiment the comparison module 236, is structured to execute the calculations used to determine the "calculated component characteristics." It is understood, however, that although the "calculated component characteristics" are determined by the comparison assembly 230, the "calculated component characteristics" are based upon measured component characteristics; thus, the "calculated component characteristics" are fixed upon the measurement of the measured component characteristics by the sensor assembly 220. Accordingly, as used herein, the "calculated component characteristics" may also be associated with the sensor assembly 220 and may be generated by the sensor assembly 220. In an alternative embodiment, the sensor assembly 220 includes a sensor module 222 that is structured to perform the calculation needed to generate "calculated component characteristics."

The comparison assembly 230, and in an exemplary embodiment the comparison module 236, is in electronic communication with the record assembly 210 and is structured to access the selected nominal data within the record assembly 210. The comparison assembly 230, and in an exemplary embodiment the comparison module 236, is further structured to compare the actual component characteristics and the selected nominal data and to communicate a signal to an output device 242, discussed below. For example, the comparison assembly 230, and in an exemplary embodiment the comparison module 236, is structured to compare the actual component characteristics and the selected nominal data so as to determine the remaining useful life for a selected circuit breaker component 28 and to provide an indication signal representing an indication of remaining useful life for a selected operating mechanism component 28. The indication of remaining useful life is, in an exemplary embodiment, calculated according to the equation which may take the generalized linear or non-linear format given below, but not limited to the following, identified as Equation A:

$$y = T\beta + \varepsilon \quad \quad \text{Equation A}$$

or $$y_1 = \beta_1 f_1(t_1) + \beta_2 f_2(t_2) + \beta_3 f_3(t_3) + \ldots + \beta_k f_k(t_k) + \varepsilon_1$$

or $$y_1 = \beta_1 f_1(x_1) + \beta_2 f_2(x_2) + \beta_3 f_3(x_3) + \ldots + \beta_k f_k(x_k) + \varepsilon_1$$

wherein:

y=Single column vector containing raw data acquired at certain times (size: n×1) e.g., sensor monitored/derived signal of temperature, gas pressure, event timing/duration data timings etc. or, in general, any dependent variable that may or may not be measured directly but used to gauge the system health.

T=Design matrix that assigns a proper relation between dependent and independent variables (size: n×k) e.g., time function or forms of functions containing time $(t) \in (f_1(t_1), f_2(t_2), \ldots, f_k(t_k))$.

X=Design matrix that assigns a proper relation between dependent and independent variables (size: n×k)$\in (f_1(x_1), f_2(x_2), \ldots, f_k(x_k))$ where, $x_i$ represents the measurable or independent variable.

β=Vector with k parameters forming model equation= $[\beta_1 \beta_2 \ldots \beta_k]^T$, etc. are the basic functions (can take any form but finally may be fitted to the polynomial form and which vary relative to the selected component 22).

$\varepsilon \sim N(O, \sigma^2)$=independent and identically distributed random variable (iid)$\in (\varepsilon_1, \varepsilon_2, \varepsilon_3, \ldots, \varepsilon_n)$.

In an exemplary embodiment, and as a specific example, a robust polynomial model selection is used to determine the physics of failure of a transient natural convection cooled heat sink, installed on the conductor arm of the circuit breaker, and can be considered as an operating mechanism component 28. In this exemplary embodiment, temperature sensors (mounted on the conductor arms and inside the circuit breaker cabinet) and velocity sensor (mounted inside the circuit breaker cabinet) are installed. The 1D problem may be defined from the principles of heat transfer by the equation:

$$T(t) - T_\infty = \frac{b}{a} + \left(T_i - T_\infty - \frac{b}{a}\right) \exp(-at)$$

wherein:

T(t)=Temperature of the system at any given time (t in sec);

$T_i$=Initial temperature of the system (° C.);

$T_\infty$=Ambient temperature (° C.); and a and b constants determined by material properties, heat source and other transient heat transfer model constants and a priori known from the experiments in the laboratory. Further substitutions and modifications may give:

$$y_1 = \beta_0 X^0 + \beta_1 X^1 + \varepsilon_i \text{ with } \beta_0 = \frac{b}{a} \text{ and } \beta_1 = \left(T_i - T_\infty - \frac{b}{a}\right)$$

where, $X = \exp(-at)$ and $y = T(t) - T_\infty$.

The above equation is similar to the generalized linear form presented in equation A, above.

As another exemplary embodiment, and as a specific example, the temperature rise on the conductor arm of the circuit breaker is directly proportional to the square of current passing through that conductor, and directly proportional to the ambient/surrounding temperature and inversely related to the air convection around the conductor (based on forced connection heat transfer principles). Thus, an equation can be modeled as:

$$T \propto I^2; T \propto T_\infty; \text{ and } T \propto \frac{1}{u};$$

$$T = a + b \times I^2 + c \times T_\infty + \frac{d}{u}.$$

With substitutions: $\beta_0=a; \beta_1=b; \beta_2=c;$ and $\beta_3=d$, this equation again resembles the form of Equation A, above, wherein:

T=Temperature of the system at any given instant;

I=Electric current in amperes;

$T_\infty$=Ambient temperature (° C.); and u=Air velocity around the conductor (in m/s).

Figure 14A:
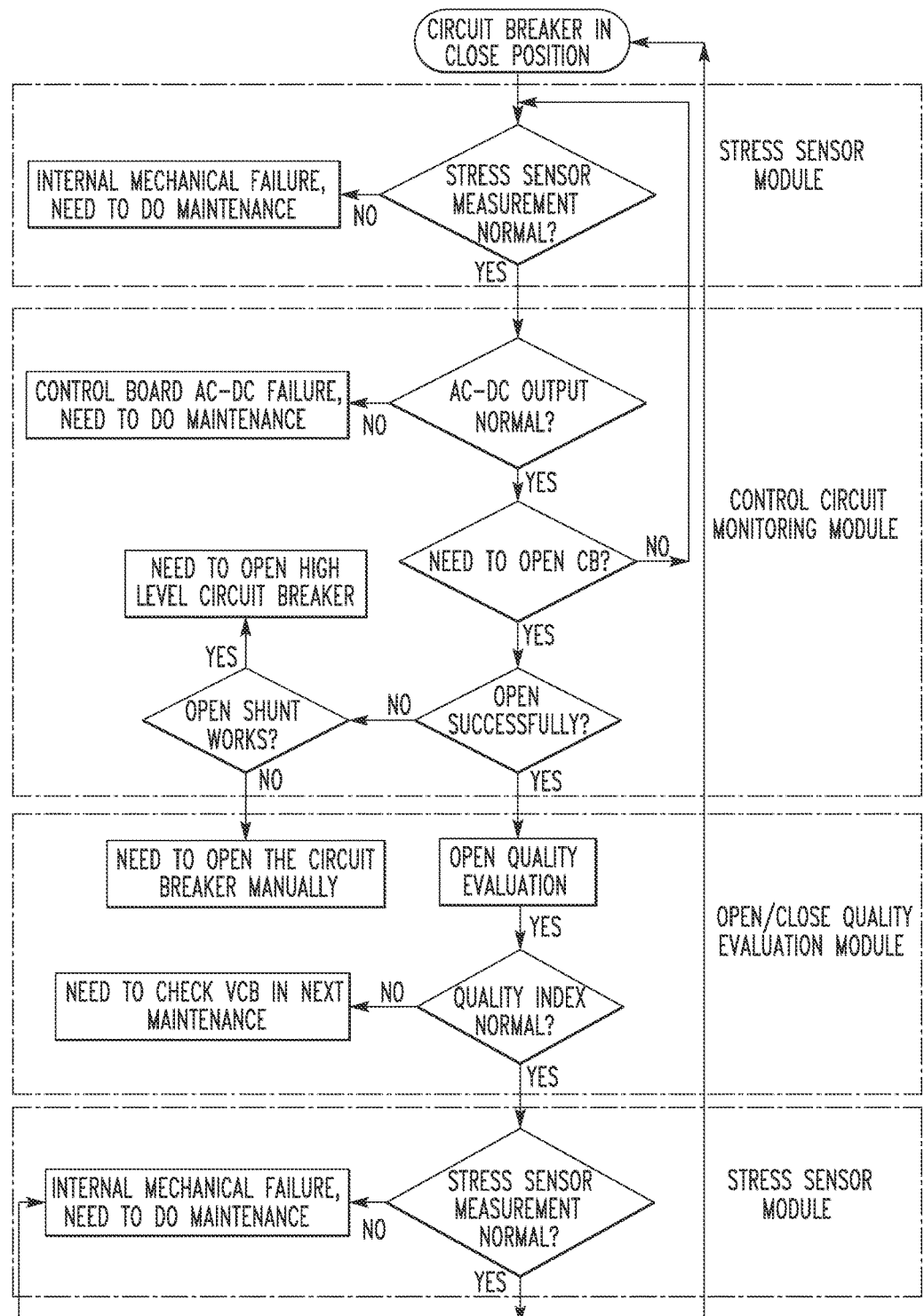
FIG. 14A is a first portion of a flow chart of the method associated with the stress sensor module, the control circuit monitoring module, the open/close evaluation module and the charging motor monitoring module.
Figure 14B:
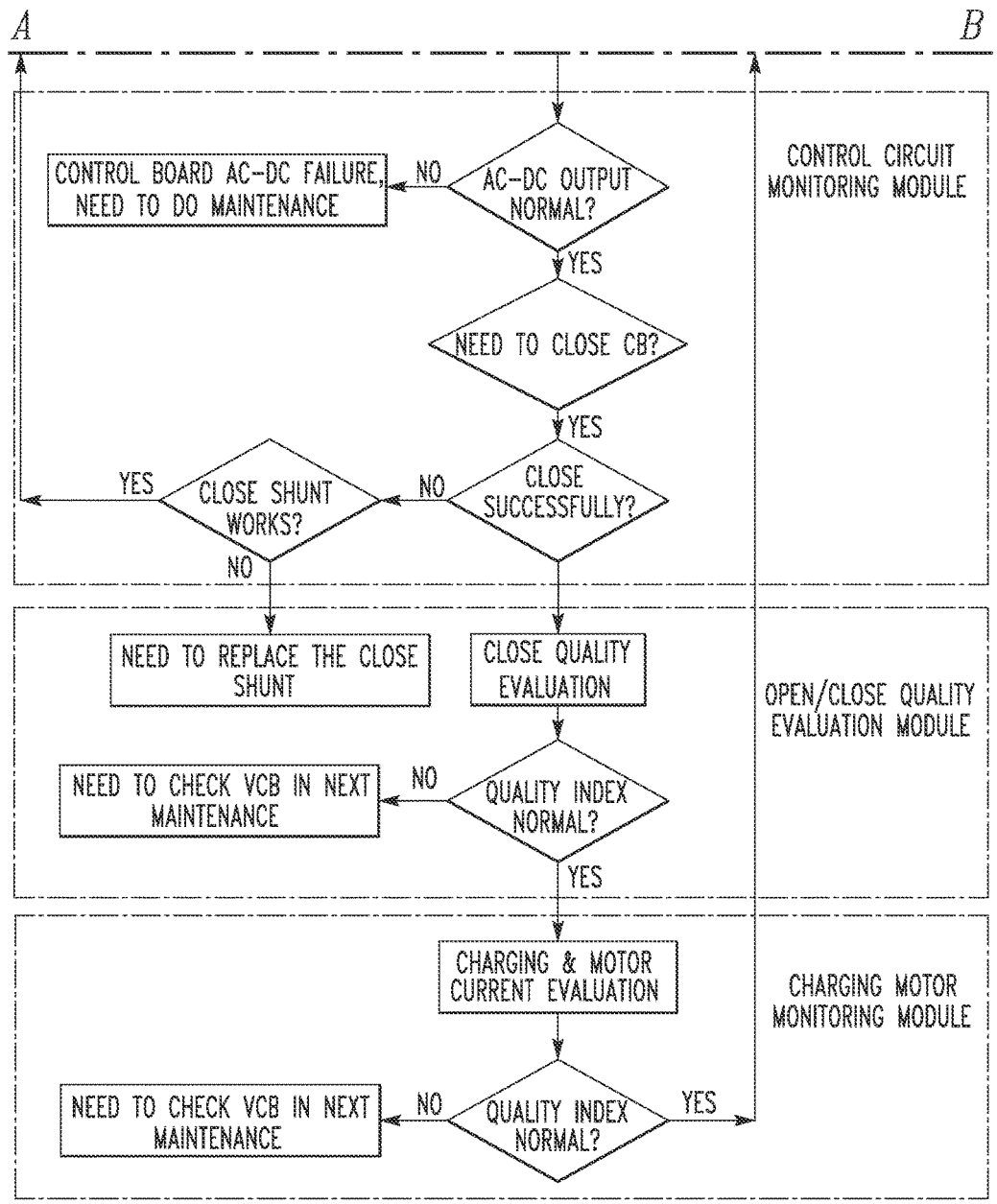
FIG. 14B is a second portion of a flow chart of the method associated with the stress sensor module, the control circuit monitoring module, the open/close evaluation module and the charging motor monitoring module.

In an exemplary embodiment, the comparison module 236 includes a stress sensor module 236A, a control circuit monitoring module 236B, an open/close evaluation module 236C and a charging motor monitoring module 236D. These modules 236A, 236B, 236C, 236D operate according to the method shown in FIGS. 14A and 14B.

The comparison assembly 230, and in an exemplary embodiment the comparison module 236, is structured to determine if the actual component characteristics are the result of sensor assembly 220 error. That is, it is known that sensor assemblies 220 may produce an erroneous result that does not reflect the actual component characteristics. These errors typically result in an unreasonable measurement and provide false positive alarm or false negative reading. The comparison module 236 is structured to identify such error by including, i.e. recording in a database, a limited acceptable range for each actual component characteristic. Any actual component characteristic that is measured beyond the limited acceptable range is ignored by the comparison module 236. The limited acceptable range for each actual component characteristic may be recorded in the database module 212.

The comparison assembly 230, and in an exemplary embodiment the comparison module 236, is further structured to provide an indication of the acceptability of the actual component characteristics when compared to the selected nominal data. That is, as used herein, "provide an indication of the acceptability of the actual component characteristics when compared to the selected nominal data" means that the comparison assembly 230 makes a determination relating to the acceptability or reliability of an operating mechanism component 28. For example, the determination, in an exemplary embodiment, relates to one of the reliability of the machine or system, the remaining useful life, the expected failure date or time to failure, or the confidence intervals of the above mentioned parameters. The indication may also be in the form of a binary selection, i.e. good or bad, yes or no, or in the form of a communication, i.e. "charging spring needs replaced."

The comparison module 236, when executed, is further structured to generate an output signal. The output signal, in an exemplary embodiment, represents indication of the acceptability of the actual component characteristics when compared to the selected nominal data. In an exemplary embodiment, the indication is in the form of an indication of remaining useful life. In an exemplary embodiment, some failure modes do not effect a singular component characteristic. Therefore, it is possible that multiple monitoring modules 236A-D can detect the possible failure mode. Mapping a relationship between the pre-trained failure mode vs. monitoring module indication can be created based on the physical circuit breaker working mechanism as well as the real measurement. The real measurement converted into the indication then can be compared to the mapping relationship.

The comparison assembly input/output device 234 is in electronic communication with the record assembly 210, the processing assembly 232 as well as all sensor assemblies 220. Thus, the comparison assembly input/output device 234 allows for communication between these elements. Further, the comparison assembly input/output device 234 is in electronic communication with the output assembly 240.

The output assembly 240 includes an output device 242, such as, but not limited to a display 244. The output assembly 240 is structured to present an indication that the actual component characteristic is either acceptable or not acceptable. For example, the indication may be an image of a green checkmark if the actual component characteristic is acceptable, or the indication may be an image of a red "X" if the actual component characteristic is not acceptable. As another example, the indication may include an image of an envelope showing an acceptable component characteristic as well as an image representing the actual component characteristic, e.g. a curve representing the actual component characteristic over a period of time. If the image representing the actual component characteristic is disposed within the envelope, the actual component characteristic is acceptable, or, if the image representing the actual component characteristic, or a portion thereof, is disposed outside the envelope, the actual component characteristic is not acceptable.

Further, the output assembly 240, in an exemplary embodiment, includes a communication assembly 260 or electronic communication between any sub-assemblies. The communication assembly 260 is structured to communicate the output signal to a remote location. The communication assembly 260 is further structured to communicate raw data or any other stored information to a remote location. The communication assembly 260 may communicate the signal via wired constructs, such as, but not limited to, fiber optics, Ethernet cables, shielded cables, CAN-BUS communication system, or wireless constructs, such as, but not limited to, Near Field Communications (NFS), blue tooth connections, WiFi connections, Radio Frequency identifications (RFID), satellite communications systems, or radio communication systems.

In an exemplary embodiment, the component monitoring system 200, or elements thereof, are modular and may be selectably coupled to a selected circuit breaker assembly. As used herein, "selectably coupled" means that two components are coupled in a manner that allows for the components to be easily decoupled without damaging the components. The record assembly 210, the comparison assembly 230, and the output assembly 240 are disposed in a modular housing assembly 300. The modular housing assembly 300 includes a number of sidewalls 302 and a selectable coupling, such as, but not limited to, a tongue and groove coupling (not shown). The modular housing assembly sidewalls 302 defines an enclosed space 306. The processing assembly 232 and other elements are disposed within the modular housing assembly enclosed space 306. For the sake of this description, the modular housing assembly 300 is identified as part of the comparison assembly 230. In this configuration, the modular housing assembly 300 may be moved between different circuit breaker assemblies 10 or various switchgear assemblies (not shown in the figure).

In an embodiment wherein the sensor assemblies 220 utilize wired communication, the modular housing assembly 300 includes a number of communication ports 310. Each modular housing assembly communication port 310 is in electronic communication with the processing assembly 232. Further, each modular housing assembly communication port 310 is structured to be in, and is placed in, electronic communication with a sensor assembly 220.

Figure 4:
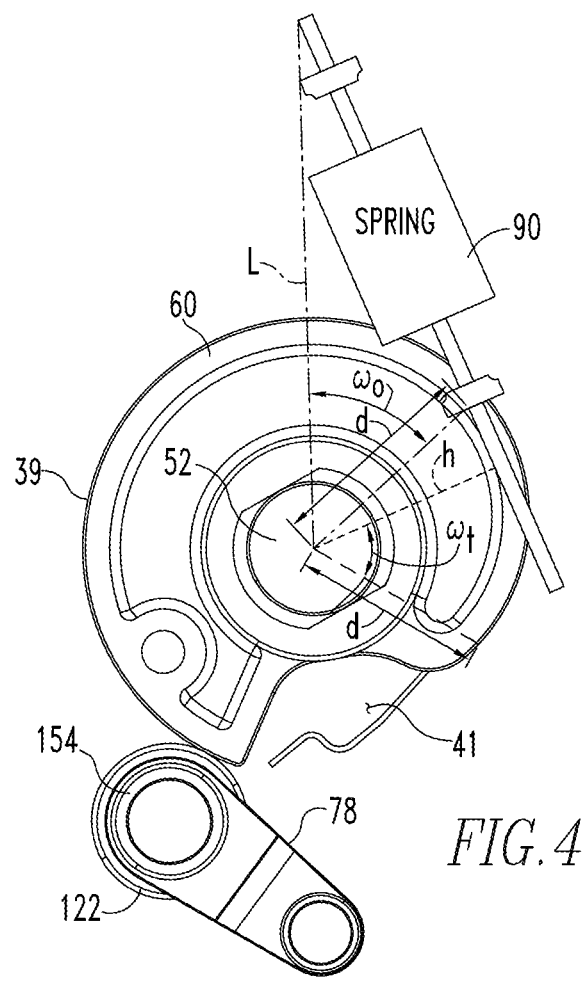
FIG. 4 is a partial side view of selected operating mechanism components with selected component characteristics.

In a specific exemplary embodiment, the component monitoring system 200, as well as the displaced component monitoring system 201, is structured to evaluate the closing spring 90 so as to determine when the closing spring 90 is worn and/or ready for replacement. In this exemplary embodiment, and as shown in FIG. 4, the following symbols are used:

L=Distance between the center of cam and the upper spring seat;

d=Distance between the center of cam and the lower spring seat;

$\omega_0$=Initial angle when closing spring fully charged;

$\omega_t$=Rotation angle when closing spring releasing energy; and h=Distance from the center of cam to the closing spring central axis.

For the configuration shown in FIG. 4, the length of charging spring at time t can be calculated as:

$$l_t = \sqrt{L^2 + d^2 - 2LD\cos(w_0 + w_t)}.$$

The spring force can be calculated as the following according to Hooke's rule:

$$F_t = (l_0 - l_t)K.$$

where K is the stiffness of the spring, and, $l_0$ is the length of closing spring in the opening condition.

The aim of this force h can be calculated as:

$$h_t = dL\sin(w_o + w_t)/l.$$

Therefore, the moment of the spring force at time t can be calculated as:

$$M_t = h_t \times F_t.$$

Figure 5:
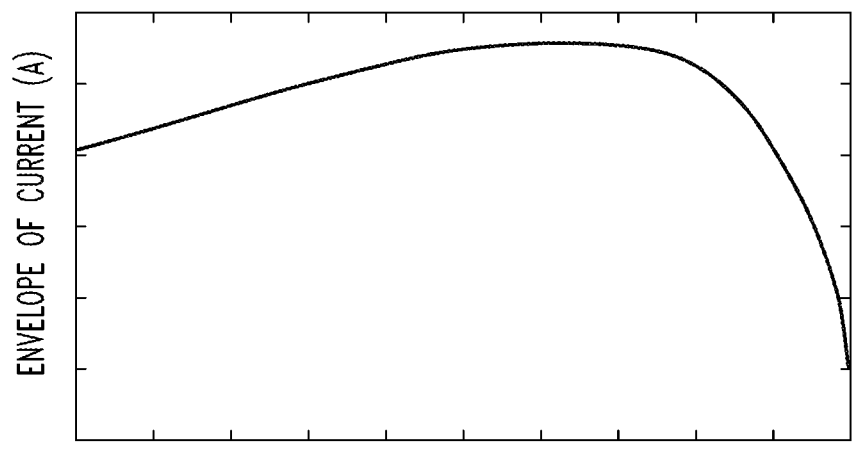
FIG. 5 is a graph showing an envelope of current and charging time.

A typical envelope of current and charging time for the first charging cam 60 is shown in FIG. 5. To match the needed torque for the first charging cam 60, the charging motor assembly 30 will output torque equivalent to the clutch and then transmit to the charging spring. Further, the charging current, i.e. the current to the charging motor assembly 30 will correspond to, i.e. change with, the changing torque. The output torque of charging motor assembly 30 can be calculated as:

$$T_t = C_m \emptyset I_t,$$

where $C_m$ is the torque coefficient, and Ø is the armature flux. Armature flux is the flux generated when excitation current flows through machine winding. The motor works in the saturation area of the flux-current curve; thus, the change of the excitation current influences the armature flux in a minor degree. Therefore, a hypothesis is raised that Ø is a constant then torque is proportional to motor current.

In an exemplary embodiment, the AC/DC converter 47 is used to power the DC motor 48 by an AC source. Thus, in this embodiment the sensor assembly 220 includes a current sensor 220' associated with, and structured to measure, the current in the AC conductor 46. The selected nominal current data for the DC current $I_t$ can be obtained by extracting the envelope of the measured AC current at the AC conductor 46. The nominal current can be obtained in the normal condition by testing the current during normal use of the circuit breaker assembly 10. Such a test is repeated several times to statistically observe and establish the nominal current. If there is no apparent fluctuation, then average current envelope after signal processing to get the final nominal current. (Alternatively, the nominal current can be established by the least square method or weighed least square method).

Further, in this exemplary embodiment, the sensor assembly 220 includes a motor output shaft torque sensor 220″ structured to measure motor output shaft torque in motor output shaft during the actuation of the DC motor 48. The torque sensor 220″ is coupled, directly coupled, or fixed to the motor assembly output shaft 50 and is structured to measure the torque therein during actuation of the charging motor assembly 30. Further, the sensor assembly 220 includes a motor timer 220‴. The motor timer 220‴ is structured to measure the time period that the charging motor assembly 30 is active, i.e. in motion. The timer 220‴, in an exemplary embodiment, is structured to detect a current in either the AC conductor 46 or the AC/DC converter 47. The timer 220‴ may be combined with the current sensor 220′.

In this embodiment, at least three component characteristics of the charging motor assembly 30 can be used to determine that a closing spring 90 is worn and/or ready for replacement. These component characteristics of the charging motor assembly 30 include, the charging time, the output energy of the charging motor assembly 30, and the correlation coefficient, as defined below. Accordingly, the current sensor 220′ is structured to measure the current in the AC conductor 46 as well as the time period the charging motor assembly 30 is actuated.

Figure 6:
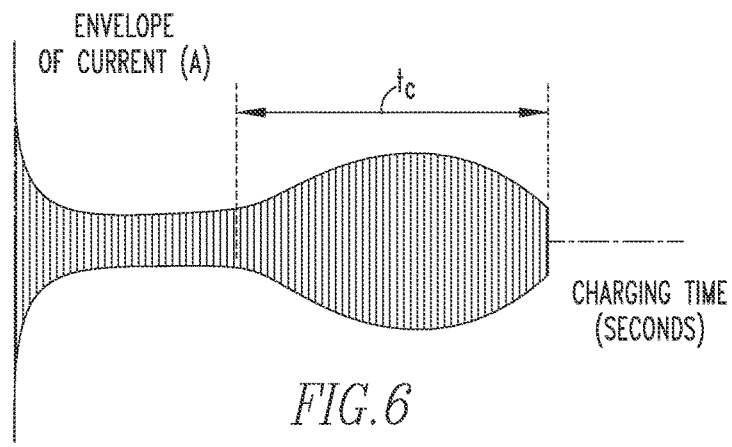
FIG. 6 is a graph showing a selected nominal time period of the charging process.
Figure 7:
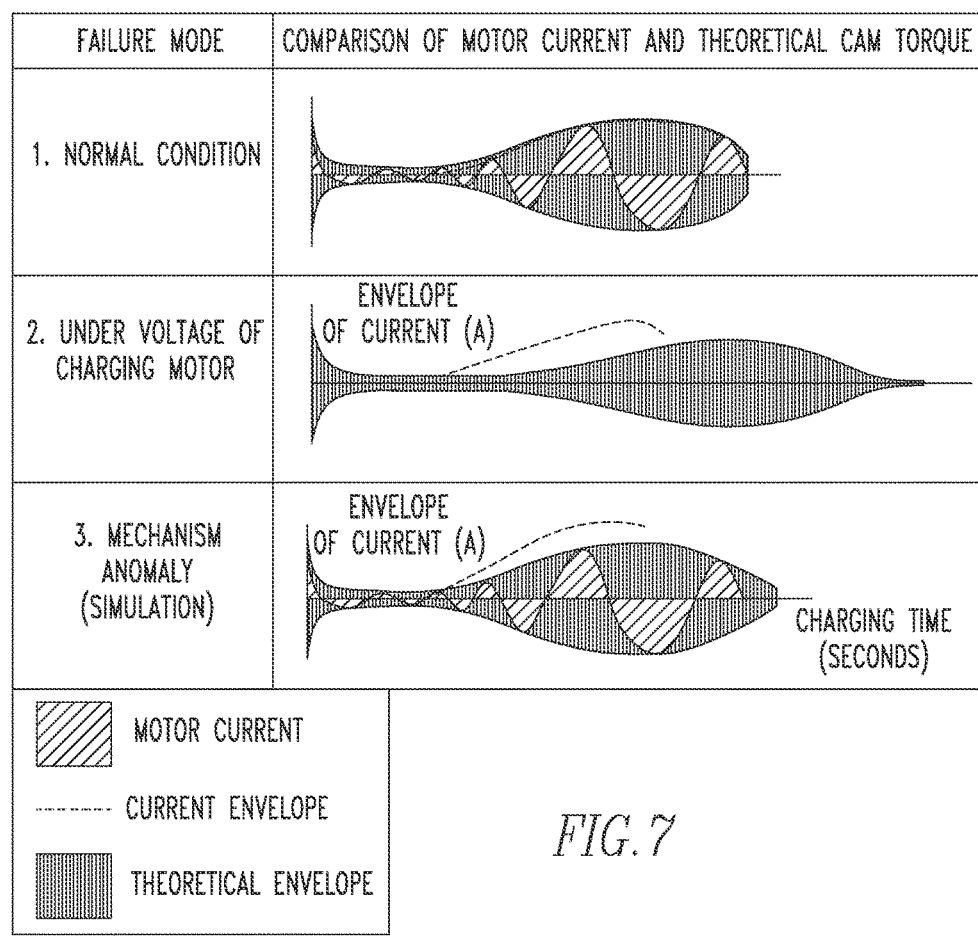
FIG. 7 is a graph showing nominal and failure mode characteristics.

A selected nominal motor charging time "$t_c$" which is determined by experimentation, is illustrated as in FIG. 6. FIG. 7 depicts a selected nominal time period of the charging process. As discussed below, if the time period of the charging process exceeds the selected nominal motor charging time, it is an indication that the external voltage is lower than required. The permitted error of the grid voltage is 7% below to 10% above. Then the permitted error of charging time can be determined. That is, for example, the energy stored by the charging spring offers the total kinetic energy to the whole system and the elastic potential energy for opening springs and contact springs. An extreme condition can be considered that if the closing spring ages with its stiffness below a certain value, the circuit breaker fails to close on command. (It can be easily seen in the torque curve.) As the stiffness decreases, the closing time will increase and influence the closing quality. Given an index indicating the closing quality and its range, the predetermined limit can be calculated in theory (or deducted by simulation). The principle of calculating the motor output torque can be extended to different types of motor and measurements.

The output energy of motor can be calculated as:

$$E=I^2Rt.$$

Considering the resistance R is a constant, the equivalent charging energy $E_1$ can be determined as:

$$E_1=E/R=I^2t.$$

The equivalent charging energy depicts how much energy the charging motor assembly 30 exerts when charging the closing spring 90 other operating mechanism components 28. The equivalent charging energy can be used as an indicator to diagnose the working condition of the operating mechanism 16, especially the stiffness of the closing spring 90. That is, as the closing spring 90 ages, the equivalent charging energy required to charge the equivalent charging energy changes. That is, for example, a spring may become less stiff if it remains charged continuously, or, a spring may become stiffer/brittle if in standby and exposed to extreme temperatures and humidity. The former is more likely than the latter. Accordingly, if the equivalent charging energy exceeds a predetermined limit, the closing spring 90 should be replaced. In this exemplary embodiment, the energy stored by the charging spring defines the total kinetic energy available to the operating mechanism 16 and the elastic potential energy for opening springs 92 and contact springs 94. An extreme condition can be considered in that, if the closing spring 90 ages with its stiffness below a certain value, the operating mechanism 16 fails to close on command, as seen in the torque curve. As the stiffness decreases, the closing time will increase and influence the closing quality. Given an index indicating the closing quality and its range, a predetermined limit can be calculated or determined by simulation.

The correlation coefficient ρ provides a correlation between charging current $I_t$ and theoretical torque $M_t$ as follows:

$$\rho = \frac{\sum (I_t - \bar{I}_t)(M_t - \bar{M}_t)}{\sqrt{\sum (I_t - \bar{I}_t)^2 \sum (M_t - \bar{M}_t)^2}}$$

wherein:

$I_t$=the value of motor current envelope in the given time domain;

$\bar{I}_t$=average of $I_t$;

$M_t$=theoretical torque provided by motor; and $\bar{M}_t$=average of $M_t$.

That is, ρ represents how well the charging process matches with the theoretical model. Thus, ρ is used as an effective index to diagnosis whether there are defects in the mechanism, especially the closing spring 90 and the first charging cam 60. This equation, again, follows the standard format of Equation A after certain transformations.

In an exemplary experiment, the motor current in three different working conditions and the extracted component characteristics, as described above, are shown below. In this exemplary experiment, the working condition is the normal condition, i.e., an external voltage of 220V, stiffness and the preload of closing spring is normal, and the clutch system is lubricated. The under voltage condition of charging motor means that the external voltage is 180V, while the other conditions remain the same. The mechanism anomaly condition means a change in the stiffness and preload in simulation, while the other conditions remain the same. The comparison of waveform can be found in FIG. 7. As is shown in FIG. 7, the measured current envelope matches well with the theoretical torque curve, and the charging time $t_c$ and charging energy E have been extracted and calculated as the reference for the normal condition. The numerical comparison is shown below.

| Mode | ρ | $t_c$(S) | $E_1$(J/Ω) |
|---|---|---|---|
| 1. Normal condition | 0.9314 | 0.097 | 1.4022 |
| 2. Under voltage of charging motor | 0.799 | 0.119 | 1.4828 |
| 3. Mechanism anomaly (simulation) | 0.7455 | 0.094 | 0.8134 |

Accordingly, the comparison indicates that, for the failure mode having an under voltage of the charging motor assembly 30, the charging time will be longer while the total output energy is similar to the total output energy calculated by theoretical curve. Whereas, for the failure mode having a mechanism anomaly, the theoretical cam torque curve changes due to the defect in the mechanism. That is, for the failure mode having a mechanism anomaly, the measured circuit envelope will not match well with the theoretical energy curve. Considering such factors, a defect in motor and charging mechanism may be detected as well as provide additional diagnosis information regarding the operating mechanism 16.

Figure 8:
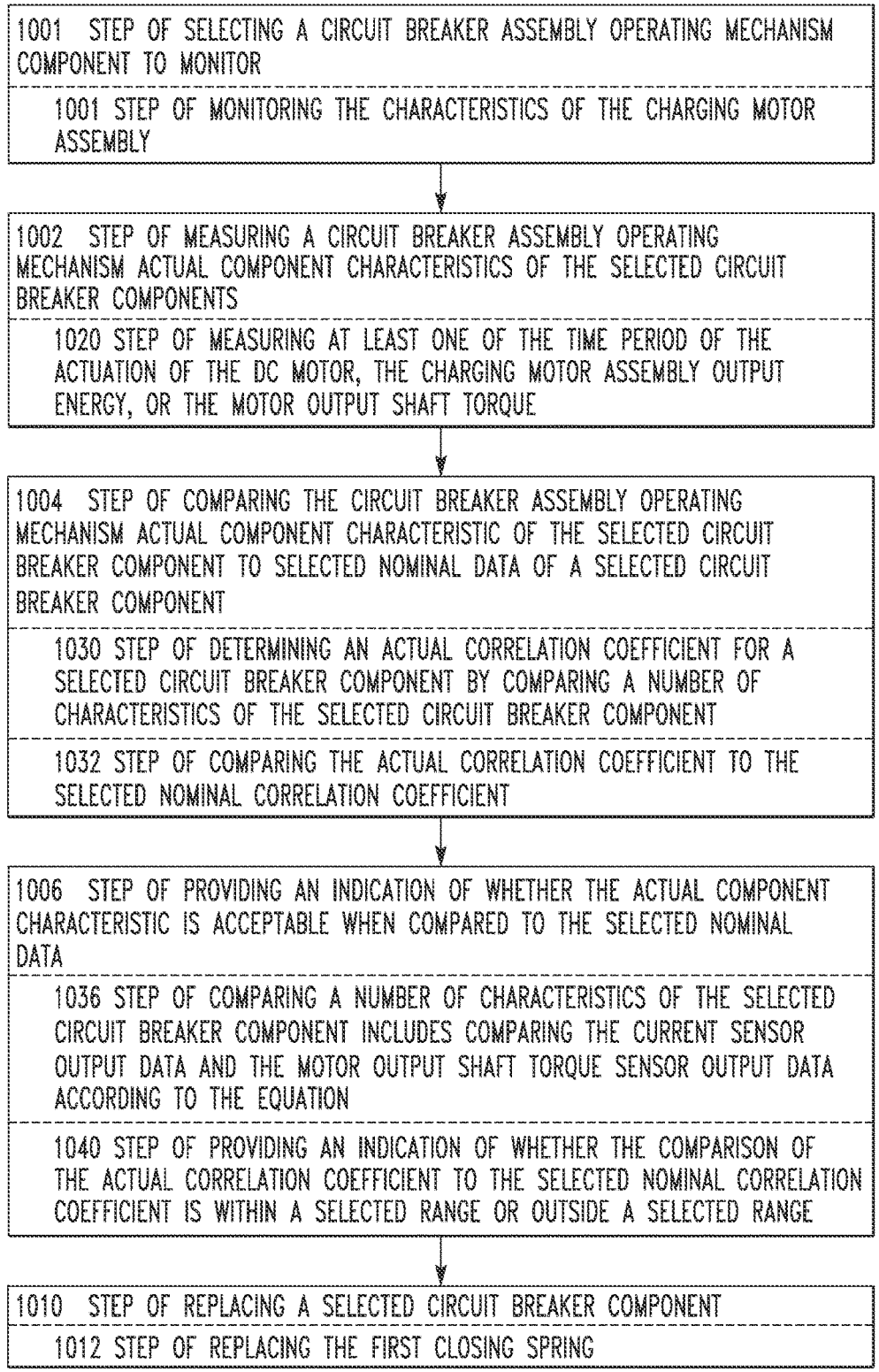
FIG. 8 is a flow chart of the disclosed method.

As shown in FIG. 8, a method of using the embodiment of the component monitoring system 200, which is also a displaced component monitoring system 201, includes selecting 1000 a circuit breaker assembly operating mechanism component 28 to monitor, measuring 1002 a circuit breaker assembly operating mechanism actual component characteristic of the selected circuit breaker component 28, comparing 1004 the circuit breaker assembly operating mechanism actual component characteristic of the selected circuit breaker component to selected nominal data of a selected circuit breaker component, providing 1006 an indication of whether the actual component characteristic is acceptable when compared to the selected nominal data, and, if the circuit breaker assembly operating mechanism actual component characteristic of a selected circuit breaker component is not acceptable when compared to the selected nominal data, then replacing 1010 a selected circuit breaker component.

In an exemplary embodiment, wherein the selected nominal data and the actual component characteristic output data are electronic constructs, it is understood that the comparing 1004 the circuit breaker assembly operating mechanism actual component characteristic of the selected circuit breaker component to selected nominal data of a selected circuit breaker component is performed by comparing the selected nominal data and the actual component characteristic output data in a computer.

In an exemplary embodiment, wherein the charging motor assembly 30 includes AC and DC components as described above, the measuring 1002 a circuit breaker assembly operating mechanism actual component characteristic of the selected circuit breaker component 28 includes measuring 1020 at least one of the time period of the actuation of the DC motor, the charging motor assembly output energy, or the motor output shaft torque.

In an exemplary embodiment wherein the record assembly 210 includes data representing a selected nominal correlation coefficient of a selected circuit breaker component, the comparing 1004 the circuit breaker assembly operating mechanism actual component characteristic of the selected circuit breaker component to selected nominal data of a selected circuit breaker component, and providing 1006 an indication of whether the actual component characteristic is acceptable when compared to the selected nominal data, and includes; determining 1030 an actual correlation coefficient for a selected circuit breaker component by comparing a number of characteristics of the selected circuit breaker component, comparing 1032 the actual correlation coefficient to the selected nominal correlation coefficient, and providing 1040 an indication of whether the comparison of the actual correlation coefficient to the selected nominal correlation coefficient is within a selected range or outside a selected range. Further, in an exemplary embodiment wherein the charging motor assembly 30 is as described above, the determining 1030 an actual correlation coefficient for a selected circuit breaker component by comparing 1036 a number of characteristics of the selected circuit breaker component includes comparing the current sensor output data and the motor output shaft torque sensor output data according to the equation:

$$\rho = \frac{\sum (I_t - \overline{I}_t)(M_t - \overline{M}_t)}{\sqrt{\sum (I_t - \overline{I}_t)^2 \sum (M_t - \overline{M}_t)^2}}$$

wherein $I_t$ is the AC current in the AC conductor during the actuation of the DC motor;

wherein $\overline{I}_t$ is the average nominal AC current in the AC conductor during the actuation of the DC motor;

wherein $M_t$ is the motor output shaft torque in the motor output shaft 50 during the actuation of the DC motor, and wherein $\overline{M}_t$ is the average motor output shaft torque in the motor output shaft 50 during the actuation of the DC motor.

Further, in an exemplary embodiment wherein the charging motor assembly 30 is as described above, the selecting 1000 a circuit breaker assembly operating mechanism component 28 to monitor, and, replacing 1010 a selected circuit breaker component includes monitoring 1001 the characteristics of the charging motor assembly 30, and, replacing 1012 the closing, first spring 90.

In another exemplary embodiment, the component monitoring system 200, as well as the displaced component monitoring system 201, is structured to evaluate the forces acting upon a latch member 44 so as to determine whether the contact spring 94 needs replaced.

The operating mechanism 16 discussed above includes two latch members 44; a close latch member 170 and a trip latch member 172. The close latch member 170 operatively engages the close latch D-shaft 126 in the manner discussed above. The trip latch member 172 operatively engages the trip latch D-shaft 124 in the manner discussed above. Thus, when the movable contact assembly 20 is in the second position, force from the contact spring(s) 94 (or other springs 34, in general) acts through the various operating mechanism components 28 on, in an exemplary embodiment, trip latch member 172. That is, as an example, the following description shall focus on the relationship between the contact spring 94 and the trip latch member 172. It is understood that other operating mechanism components 28 may be monitored to determine that status, i.e. health, of other springs 34.

Figure 9:
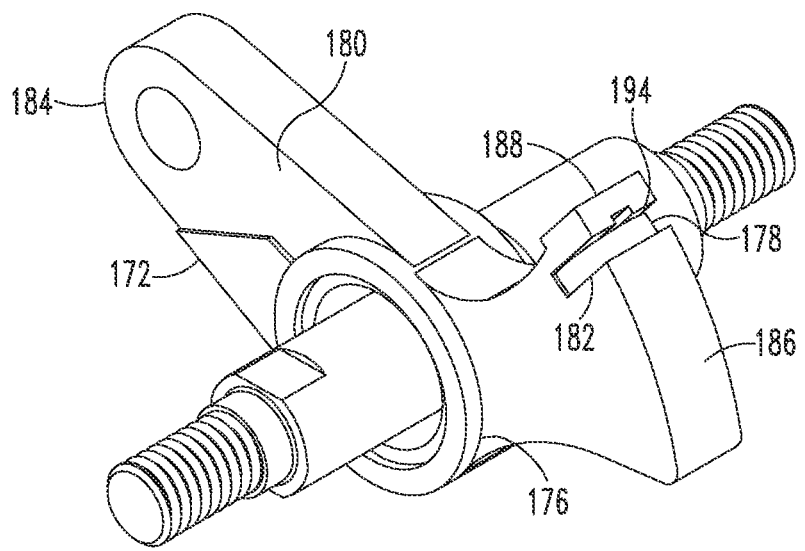
FIG. 9 is an isometric view of a monitoring latch assembly.
Figure 10:
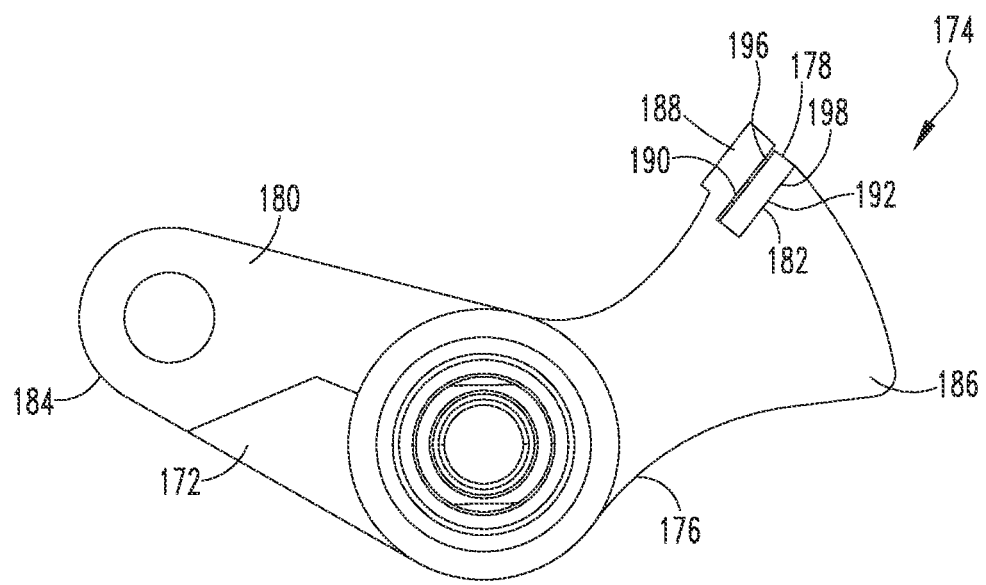
FIG. 10 is a side view of a monitoring latch assembly.

In an exemplary embodiment, the trip latch member 172 is a monitoring latch assembly 174. That is, in this exemplary embodiment, the monitoring latch assembly 174 includes a latch member 176 and a sensor assembly 178, as shown in FIGS. 9 and 10. The latch member 176 includes a body 180 defining a pocket 182. The latch member body 180 is a generally planar body including a latching first end 184 and a coupling second end 186. The latch member body second end 186 includes a latching surface 188. In an exemplary embodiment, the latch member body second end latching surface 188 is disposed on the thinner lateral surface between the wide generally planar surfaces of the generally planar latch member body 180. The latch member body pocket 182 is disposed adjacent the latch member body second end latching surface 188.

In an exemplary embodiment, the latch member body pocket 182 is sized and shaped to generally correspond to the sensor assembly 178, discussed below. Thus, in an exemplary embodiment, the latch member body pocket 182 includes a generally planar first surface 190 and a generally planar second surface 192. The latch member body pocket first surface and second surface 190, 192 are generally parallel.

Figure 11:
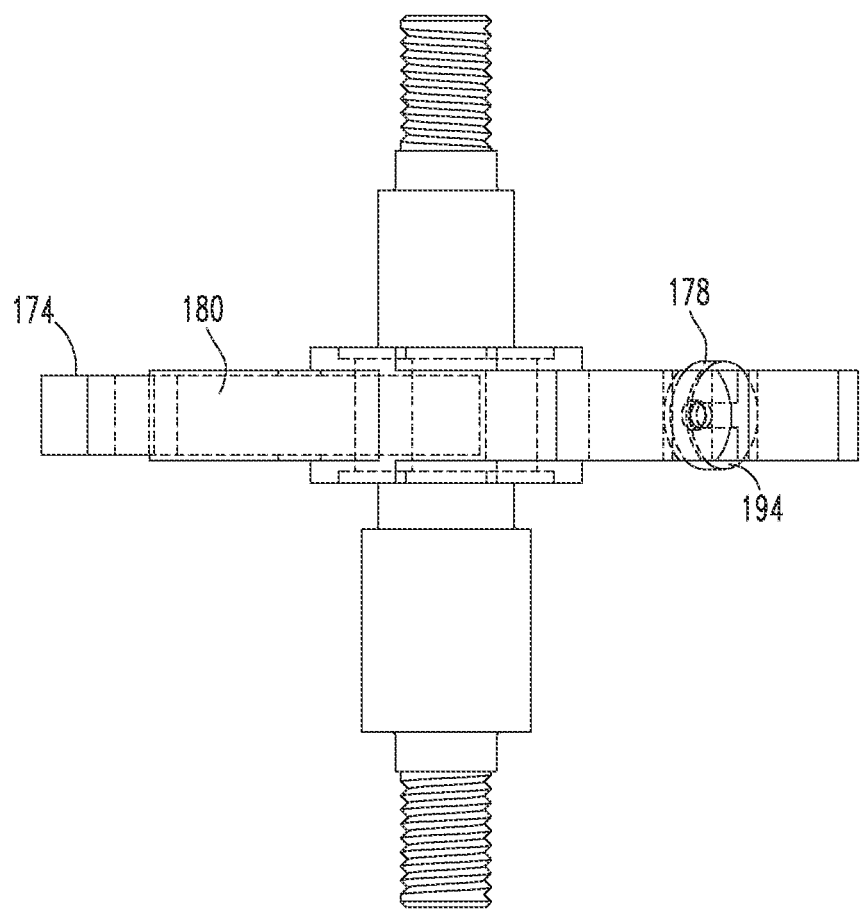

As shown in FIGS. 9-11, and in an exemplary embodiment, the sensor assembly 178 includes a disk-like body 194, which is a generally planar body. That is, the sensor assembly body 194 includes a generally planar first surface 196 and a generally planar second surface 198. When the sensor assembly body 194 is disposed in the latch member body pocket 182, the sensor assembly body first surface 196 is coupled, directly coupled, or engagingly coupled to the latch member body pocket first surface 190. Similarly, when sensor assembly body 194 is disposed in the latch member body pocket 182, the sensor assembly body second surface 198 is coupled, directly coupled, or engagingly coupled to the latch member body pocket second surface 192. In an exemplary embodiment, the sensor assembly 178 is structured to measure at least one of a static pressure or a deformation.

Figure 2A:
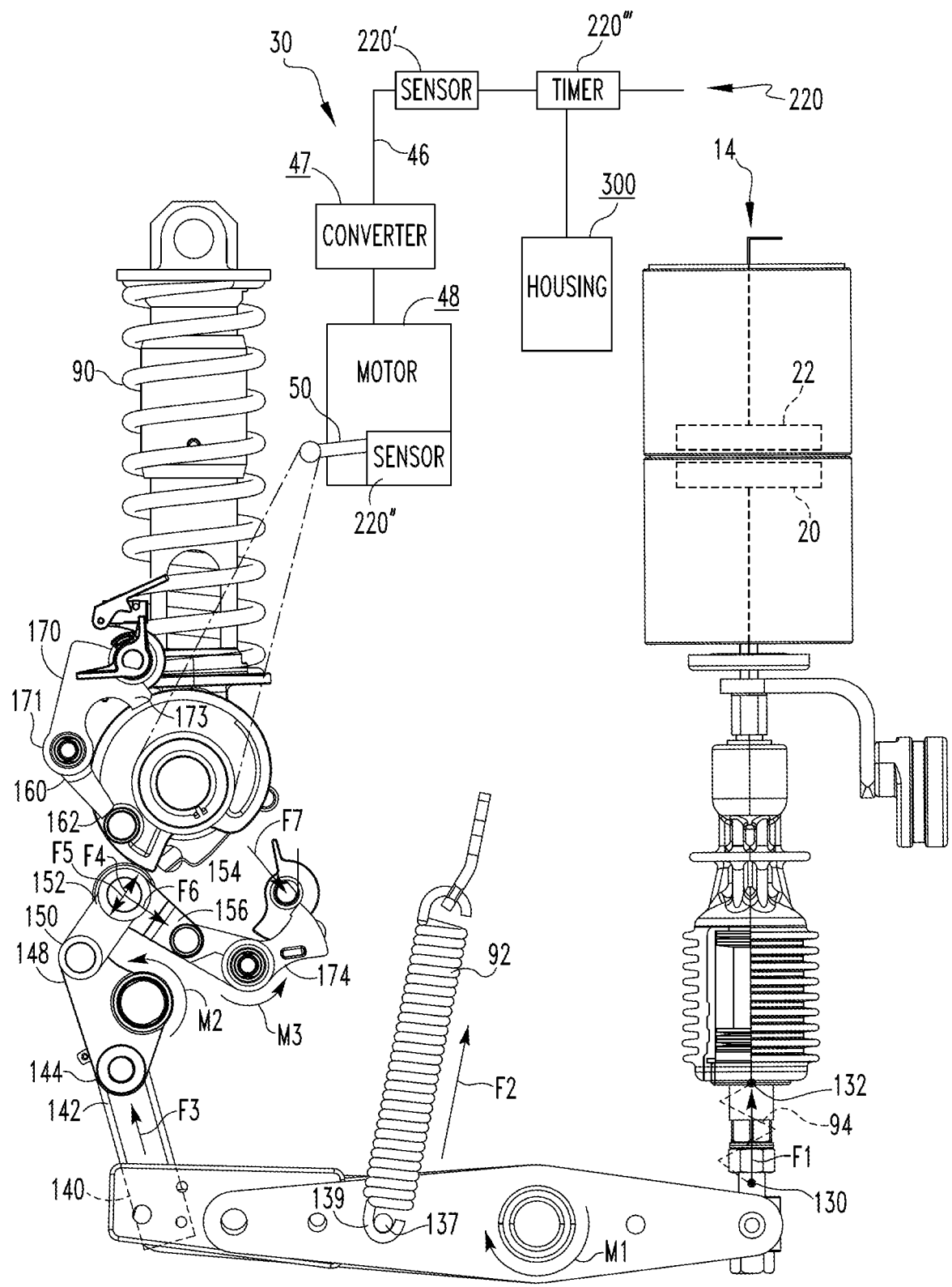
FIG. 2A is a side view of a circuit breaker assembly.

As noted above, in this exemplary embodiment, the component monitoring system 200, as well as the displaced component monitoring system 201, is structured to evaluate the forces acting upon a latch member 44 so as to determine whether the springs 34, including but not limited to close spring 90, open spring 92, and/or contact spring 94, needs replaced. Thus, in this embodiment, the record assembly 210 includes a desired range for the force acting upon the latch member body 180. That is, in the configuration described above, the operating mechanism components 28 generate a number of forces and moments as shown in FIG. 2A. These forces and moments include:

F1—The force generated by the contact spring 94;
F2—The force generated by the opening spring 92;
F3—The force acting on the lay shaft casting link member 76 by the first link member 74;
F4—The force acting on the first charging cam 60 by main roller 122;
F5—The force acting on the lay shaft casting link member 76 by the main link coupler member 77;
F6—The force acting on the trip latch member 172 by the main link member 78;
F7—The force acting on the trip latch member 172 by trip latch D-shaft 124;
M1—The moment about rocker link shaft 54;
M2—The moment about lay shaft 56; and
M3—The moment about trip latch shaft 59.

Figure 12:
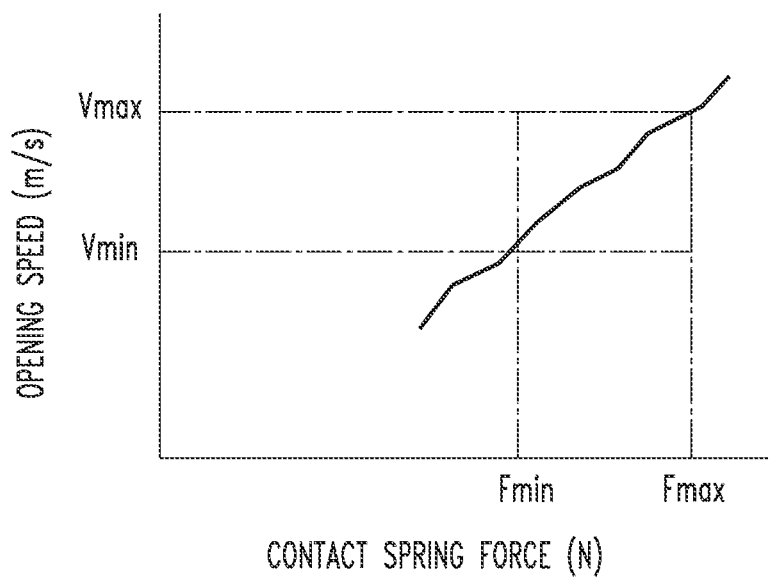
FIG. 12 is graph showing a relationship between the opening speed of the movable contact assembly and the contact spring force.
Figure 13:
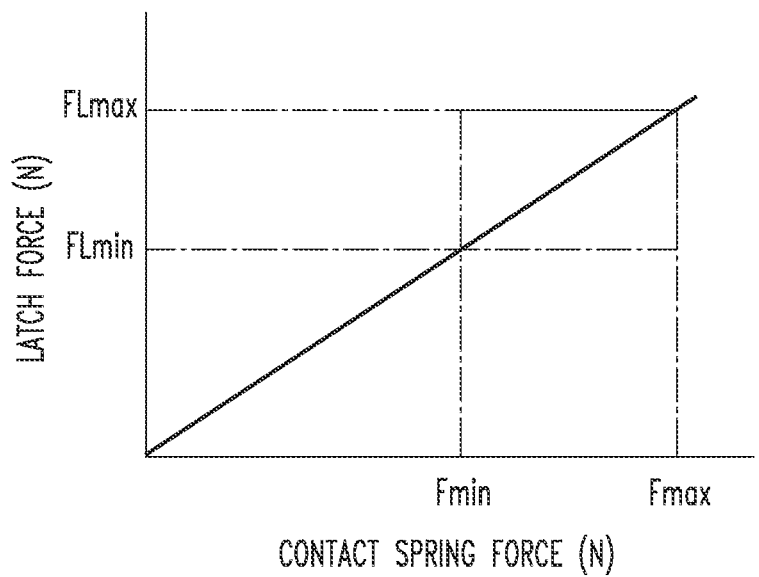
FIG. 13 is a graph showing a relationship between the latch force and the contact spring force.

Knowing the characteristics, e.g. geometries, materials, positions, etc. of the various operating mechanism components 28, the various forces and moments above may be calculated. Moreover, as shown in FIGS. 12 and 13, the operating mechanism 16 may be tested so as to establish a relationship (1) between the opening speed of the movable contact assembly 20 and the contact spring 94 force (F1), and, (2) the latch force (F7) and the contact spring 94. Moreover, an acceptable range for the opening speed of the movable contact assembly 20, the contact spring 94 force (F1), and, (2) the latch force (F7) can be established. That is, these values can be initially calculated in a theoretical model. Given the parameters of geometry and material, the transmission ratio and equivalent mass can be determined approximately. Then, the mechanical characteristics including opening and closing time, and the force in the structure can be determined. Applying the simulation method is used to double check the accuracy of established model. Finally, experiments verify the ideal model and then, by comparison, determine the threshold of each physical quantity in a certain margin. For example, the latch force is calculated by assuming a rotational equilibrium. In that case, the $\Sigma M$ of latch with respect to a rotating bearing (not shown) is zero (0). Since the latch force is measured by the sensor, the interaction force added to the spring 94 can then be determined given a geometric measurement.

Accordingly, by measuring the latch force (F7) and comparing that to the selected nominal data for the latch force (F7), the need to replace the contact spring 94 may be determined.

In another exemplary embodiment, the component monitoring system 200, or displaced component monitoring system 201, includes a number of vibration sensor assemblies 320 as well as other sensor assemblies 220. In this embodiment, the component monitoring system 200 includes a record assembly 210 a comparison assembly 230, and an output assembly 240 which operate as discussed above. That is, for example, the vibration sensor assemblies 320 as well as other sensor assemblies 220 are in electronic communication with the comparison assembly 230, as discussed above.

As used herein, a "vibration sensor assembly" is a sensor assembly structured to detect vibrations or acceleration in a component, an assembly, a group of components or assemblies, a substantial portion of the circuit breaker assembly 10, or the entire circuit breaker assembly 10. A vibration sensor assembly 320 is structured to detect vibrations and it is understood that vibrations may affect more than one component. Hereinafter, an exemplary vibration sensor assembly 320 will be discussed in relation to, i.e. is structured to detect vibrations in, a substantial portion of the circuit breaker assembly 10. It is understood that this is merely the example used herein and is not limiting. A vibration sensor assembly 320 includes, but is not limited to, accelerometers. It is further understood that in an exemplary embodiment, the vibration sensor assembly 320 is structured to measure vibration data relative to time; that is, a vibration sensor assembly 320 includes a chronometer. The other sensor assemblies 220 used in this embodiment are structured to detect a gap voltage and a trip coil current. In an exemplary embodiment, the gap voltage sensor assembly 220 and a trip coil current sensor assembly 220 also include a chronometer. It is understood the time keeping function may be performed by other elements of the component monitoring system 200 such as, but not limited to, the record assembly 210.

In an exemplary embodiment, a number of vibration sensor assemblies 320 are coupled, directly coupled, removably coupled or fixed to the circuit breaker assembly housing assembly 12. The vibration sensor assemblies 320 are structured to detect problems with a number of circuit breaker assembly 10 components and as such are, in an exemplary embodiment, part of a displaced component monitoring systems 201. That is, as noted above, the operating mechanism 16 includes a number of components 28. Some of the operating mechanism components 28 are discussed above. It is further noted that the operating mechanism components 28 further include a charging pawl and gear teeth, as well as lubrication (none shown). That is, as used herein, the lubrication used in conjunction with the operating mechanism 16 is an operating mechanism component 28. In the disclosed exemplary embodiment, the vibration sensor assembly 320 is structured to detect problems with the charging pawl, gear teeth, lubrication, the charging motor assembly 30, and selected cam members 32. Further, in an exemplary embodiment, as shown, there are three vibration sensor assemblies 320, 320', 320" (shown schematically) that are spaced from each other, i.e coupled, directly coupled, or fixed to different areas of the circuit breaker assembly 10. Further, in an exemplary embodiment, each vibration sensor assemblies 320, 320', 320" is structured to measure vibrations primarily in one direction (as shown in FIG. 1 by the arrow associated with each sensor) corresponding to an axis of a Cartesian coordinate system. Further, in this configuration, data from the three vibration sensor assemblies 320, 320', 320" may be compared to each other.

Vibrations of any component, assembly, or in this exemplary embodiment, a substantial portion of the circuit breaker assembly 10, are, as used herein, an "actual component characteristic" (discussed above). As with the sensor assembly 220 described above, a vibration sensor assembly 320 includes, or is structured to be coupled to and in electronic communication with, a power source (not shown). Further, a vibration sensor assembly 320 is further structured to transmit output data representing the circuit breaker component's actual component characteristic which is identified herein as "actual component characteristic output data" (discussed above). As before, and in an exemplary embodiment, the actual component characteristic output data signal has characteristics of between about 0-10V DC, between about 4-20 mA and between about 100-1000 Hz, or, digital signal output.

Thus, as is known, elements of the circuit breaker assembly 10, such as, but not limited to the operating mechanism 16 and the movable contact assembly 20, move between known configurations and positions during the operation of the circuit breaker assembly 10. The configurations and positions include the first and second positions noted above as well as positions and configurations associated with charging the closing spring 90. By way of non-limiting example, a circuit breaker assembly 10 may move through a sequence such as charge-close-charge-open-close-open wherein "charging" relates to the closing spring 90 and "open" and "close" relate to the position of the operating mechanism 16 and the movable contact assembly 20.

Figure 15:
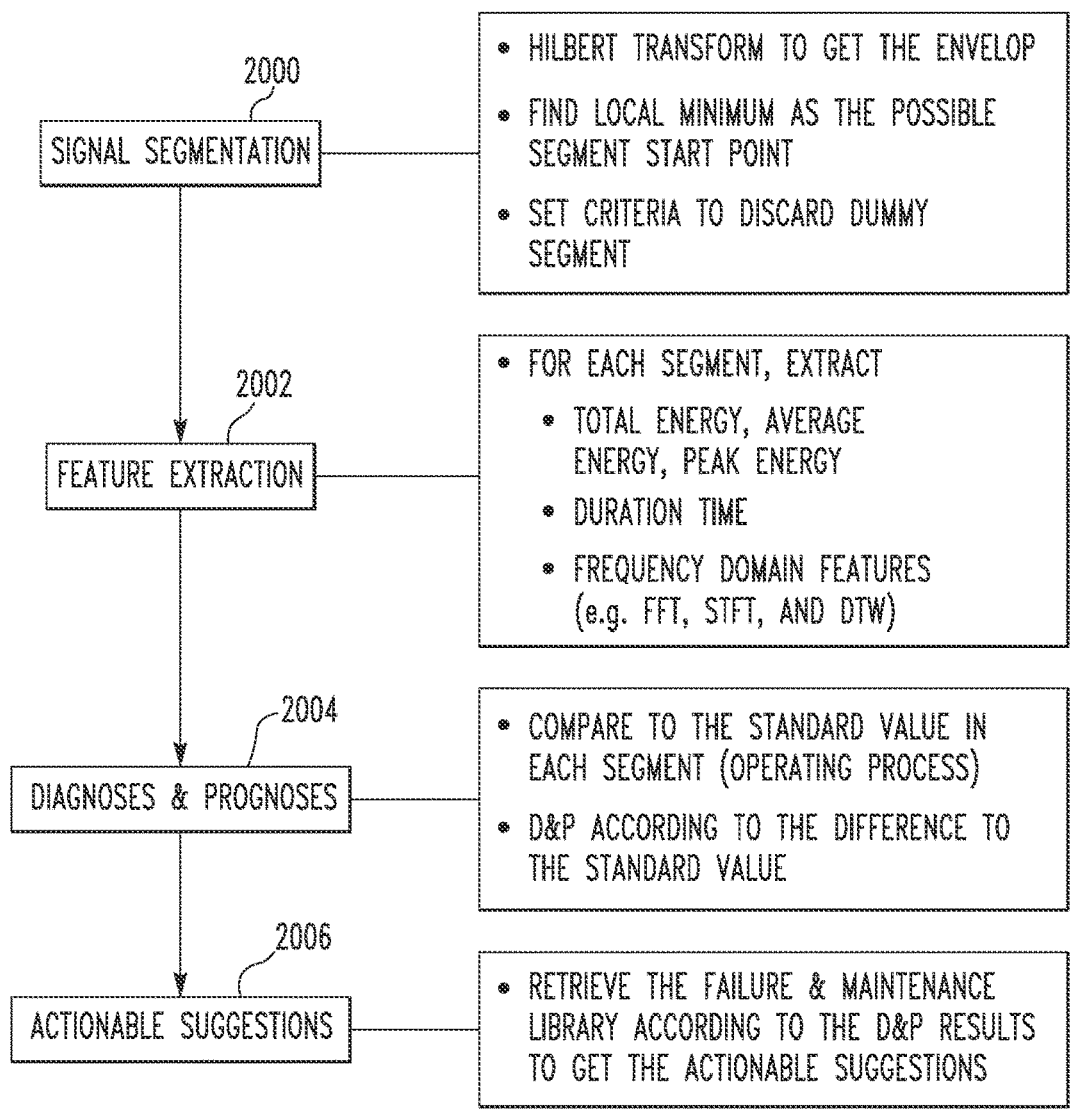
FIG. 15 is a flow chart showing the steps for vibration based diagnosis and prognosis.

In this exemplary embodiment, the record assembly 210, and in an exemplary embodiment the database module 212, includes data representing selected nominal data includes "model selected nominal data." As used herein, "model selected nominal data" is data determined via testing of a "masterpiece circuit breaker." As used herein, a "masterpiece circuit breaker" is a circuit breaker assembly that is maintained in an operational and like new condition. The method of vibration based diagnosis and prognosis is initially performed on a masterpiece circuit breaker and used to generate the model selected nominal data. The model selected nominal data includes data representing the vibrations associated with a masterpiece circuit breaker assembly 10 as the components move into the various positions and during operations such as, but not limited to, charging the closing spring 90. The same, or a substantially similar analysis is then performed on an in use circuit breaker assembly 10 to generate actual component characteristic output data and then to calculate calculated component characteristics. The method for vibration based diagnosis and prognosis is shown in FIG. 15.

Generally, the method includes performing signal segmentation 2000, performing feature extraction 2002, performing diagnosis and prognosis 2004, and providing actionable suggestions 2006. The steps shown on the left are the primary steps with the sub-steps of each shown to the right.

In an exemplary embodiment, the comparison assembly 230 is structured to initially performing signal segmentation 2000 on the actual component characteristic output data thereby creating signal data segments. That is, the actual component characteristic output data measured on the masterpiece circuit breaker is an electronic construct such as, but not limited to, a signal. Further, the signal includes data representing time. Thus, the signal, i.e. the signal is capable of being "segmented," i.e. broken into distinct periods of time. Thus, the model selected nominal data includes "segmented signal data." That is, as used herein, "segmented signal data" means a number of portions of data measured over a period of time. Further, each portion of data for a specific period of time is, as used herein, a "data segment." Thus, "segmented signal data" includes a number of "data segments." In an exemplary embodiment, the identified data segments are associated with each separate phase of the charge-close-charge-open-close-open sequence discussed above. Further, each segment includes time component.

Figure 16:
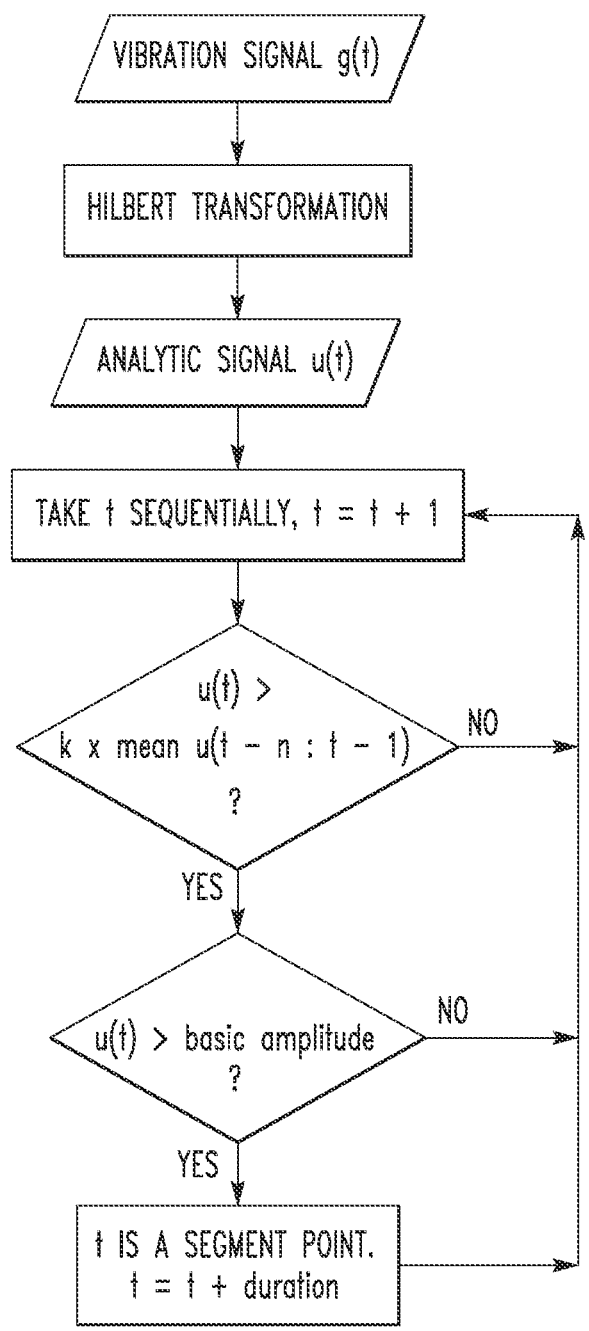
FIG. 16 is a flow chart showing the steps for signal segmentation.

As shown in FIG. 16, the comparison assembly 230 is structured to perform a signal segmentation including acquiring actual component characteristic output data. This process includes acquiring the actual component characteristic output data 2020, performing a Hilbert transformation to establish an envelope 2022 and establishing time for each local minimum vibration 2024, which indicates the start of a new measure period. To avoid capturing zero point as the local minimum, it is better to extract the envelope of original signal. The envelope can be calculated from the analytic signal by Hilbert transform of original signal. In FIG. 16, analytic signal u(t) is obtained through Hilbert transform of original signal g(t), which is a complex-valued function that has no negative frequency components. The envelope of analytic signal is the sum of the squares of real part and imaginary part. Further, FIG. 16 is a detailed explanation of performing signal segmentation 2000 (FIG. 15). That is, at "take t sequentially, t=t+1", the sensors record the local maximum on the envelope of u(t). If u(t)<k*mean value of previous n, where k is a pre-set scaling parameter to the mean value, and u(t) is larger than the basic amplitude, which is also a pre-set parameter, then the current t is a point for segmentation. The step of u(t)>basic amplitude is the criteria to discard the dummy segment points.

It is understood that when this step is performed on a masterpiece circuit breaker, the comparison assembly 230 establishes the "segments," discussed above. Further, in an exemplary embodiment, the comparison assembly 230 is structured to discard dummy segment points 2026 (FIG. 15) Within each segment, when performed on a masterpiece circuit breaker, the comparison assembly 230 is structured to perform feature extraction 2002. The extracted features include a total energy characteristic, a segment mean energy attribute, a segment duration attribute, and a time domain correlation attribute. The attributes are established according to the following:

| Features | Meaning | Equation |
|---|---|---|
| $E_{total}$ | Total energy in each segment | $E_{total} = \Sigma_{i=1}^{N} \|u_i\|^2$ |
| $\bar{E}$ | Segment mean energy | $\bar{E} = \frac{1}{N}\Sigma_{i=1}^{N} \|u_i\|^2$ |
| T | Segment duration | $T_n = t_{start\ point\ of\ n+1} - t_{start\ point\ of\ n}$ |
| $C_t$ | Time domain correlation | $C_t = \frac{1}{N}\Sigma_{i=1}^{N}(u_i - \bar{u})(u_i^{standard} - \bar{u}^{standard})$ |

Each segment of vibration corresponds to a major collision in mechanism, and the features extracted from each segment can also represent the property of collision. $E_{total}$ presents the total energy in each segment. $E_{total}$ is related to the collision intensity and the time duration. $\bar{E}$ is the average energy in each segment, which is only related to the collision intensity. T is the segment duration, which represents how long a collision lasts until the next collision happens. $C_t$ is a correlation number between the measured signal and the standard signal in each segment. $C_t$ represents the similarity between the measured signal and the signal in a "healthy" circuit breaker.

It is understood that the total energy attribute, the segment mean energy attribute, the segment duration attribute, and the time domain correlation attribute are defined as a range or a limit selected by the user. That is, the selected range or limit based upon the total energy attribute, the segment mean energy attribute, the segment duration attribute, and the time domain correlation attribute are selected as the model selected nominal data. Further, each of the total energy attribute, segment mean energy attribute, segment duration attribute, and time domain correlation attribute are calculated by methods such as, but not limited to, Fast Fourier transform (FFT), Short-time Fourier transform (STFT), Dynamic Time Warping (DTW) data.

Figure 17:
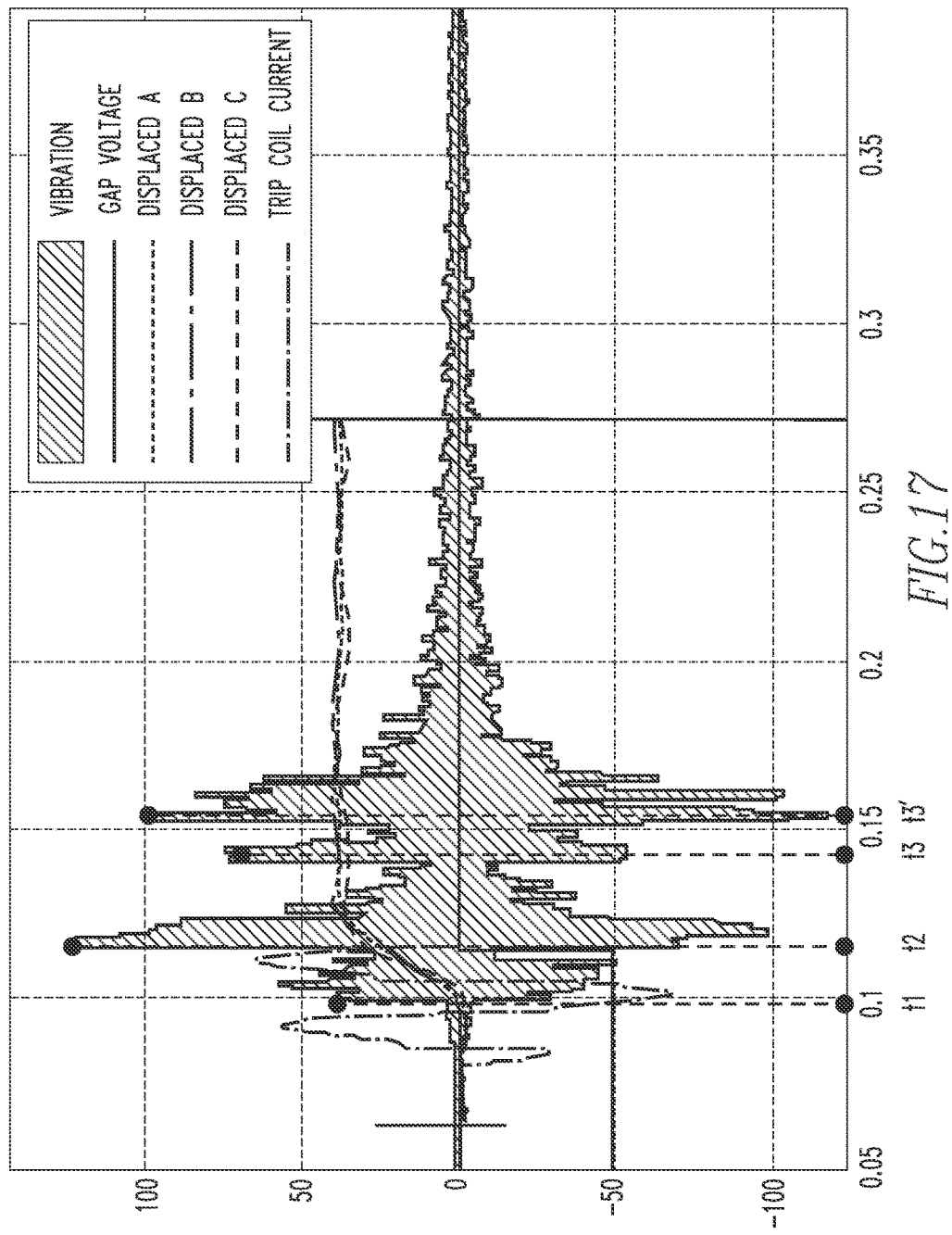
FIG. 17 is a graph of exemplary model selected nominal data for the vibrations associated with a masterpiece circuit breaker during a closing operation.

Exemplary model selected nominal data for the vibrations associated with a masterpiece circuit breaker during a closing operation are shown in FIG. 17. In an exemplary embodiment, the model selected nominal data further includes data representing the gap voltage, trip coil current, the displacement signal associated with the electrode of Phase A, the displacement signal associated with the electrode of Phase B, and the displacement signal associated with the electrode of Phase C, hereinafter "Displacement A," "Displacement B," and "Displacement C," respectively. The gap voltage is the voltage between the upper and lower electrodes, which represents whether the circuit breaker is in an open or close position. The displacement is for the lower electrode with regards to its closed position, and the annotation A, B, C are for three phases.

As shown in FIG. 17, the three time segments are associated with exemplary physical processes and identified as t1, t2, and t3, as well as t3', t3", etc. as the spring oscillates. The first segment, t1, is associated with the cam 32 and roller 120 impact; the second segment, t2, is associated with the collision (and reduction of velocity to zero) of the of the contact assemblies 20, 22; and, segment t3 is associated with the oscillation of the one or more spring 34. Alternatively, in another graph (not shown) time segments t1, t2, and t3 may be associated with different exemplary physical processes. That is, t1 may be associated with the end of the over travel; t2 may be associated with damper (not shown) impact, and t3 may be associated with the end on the opening operation.

During operation of the circuit breaker assembly 10, the vibration sensor assemblies 320, as well as other sensor assemblies 220 noted above, are used in the same process or method to generate actual component characteristics that is compared to the model selected nominal data. That is, the comparison assembly 230 is structured to record the actual component characteristic output data and then to calculate calculated component characteristics. The calculated component characteristics, which are also actual component characteristics, are compared to the model selected nominal data. In this embodiment, the comparison assembly 230 is structured to compare the actual component characteristics, i.e. the calculated component characteristics, to the model selected nominal data. As named herein, the calculated component characteristics shall be identified as the total energy characteristic, the segment mean energy characteristic, the segment duration characteristic, and the time domain correlation characteristic, discussed below. The "characteristics" correspond to the "attributes" discussed above. That is, the "attributes" are the actual/calculated component characteristics for a masterpiece circuit breaker and the "characteristics" are the actual/calculated component characteristics for a circuit breaker assembly 10 that is in use.

As stated above, the comparison assembly 230 is structured to compare the calculated component characteristics to the model selected nominal data. That is, the comparison assembly 230 is structured to compare, within each measured period and segmented signal data segment, the total energy characteristic to the total energy attribute, the segment mean energy characteristic to the segment mean energy attribute, the segment duration characteristic to the segment duration attribute, and the time domain correlation characteristic to the time domain correlation attribute.

In this embodiment, Equation A (above) may be expressed as:

$$y_1 = \beta_1 f_1(t_1) + \beta_2 f_2(t_2) + \beta_3 f_3(t_3) + \ldots + \beta_k f_k(t_k) + \ldots + \varepsilon_i.$$
Or, $$y_1 = \beta_1 f_1(t_1, t_2, t_3 \ldots t_n) + \beta_2 f_2(t_1, t_2, t_3, \ldots t_n) + \ldots + \varepsilon_i.$$
Or, $$y_1 = \beta_1 f'_1(t_1, t_2, t_3, \ldots t_n) + \beta_2 f'_2(t_1, t_2, t_3, \ldots t_n) + \ldots + \varepsilon_i. \text{ Or}$$

$$y_i = \beta_1 f_1(x_1, x_2, \ldots) + \beta_2 f_2(x_1, x_2, \ldots) + \ldots + \beta_k f_k(x_1, x_2, \ldots) + \ldots + \varepsilon_i; \text{ Or, in general format:}$$

$$y = T\beta + \varepsilon \text{ or } y = X\beta + \varepsilon \text{ wherein;}$$

y=a form containing actual component characteristic output data $\in (y_1, y_2, \ldots, y_n)$ size (n×1);

T=a form assigning relation between time function and actual component characteristic output data $\in (f_1(t_i), f_2(t_i), \ldots, f_k(t_i))$;

X=a form assigning relation between independent variables and actual component characteristic output data $\in (f_1(x_1), f_2(x_2), \ldots, f_k(x_k))$;

β=a form with k parameters forming model equation= $[\beta_1 \beta_2 \ldots \beta_k]^T$ and k=total number of characteristic output parameters for which the data is collected; and $\varepsilon \sim N(O, \sigma^2)$=independent and identically distributed random variable (iid) $\in (\varepsilon_1, \varepsilon_2, \varepsilon_3, \ldots, \varepsilon_n)$.

Figure 18A:
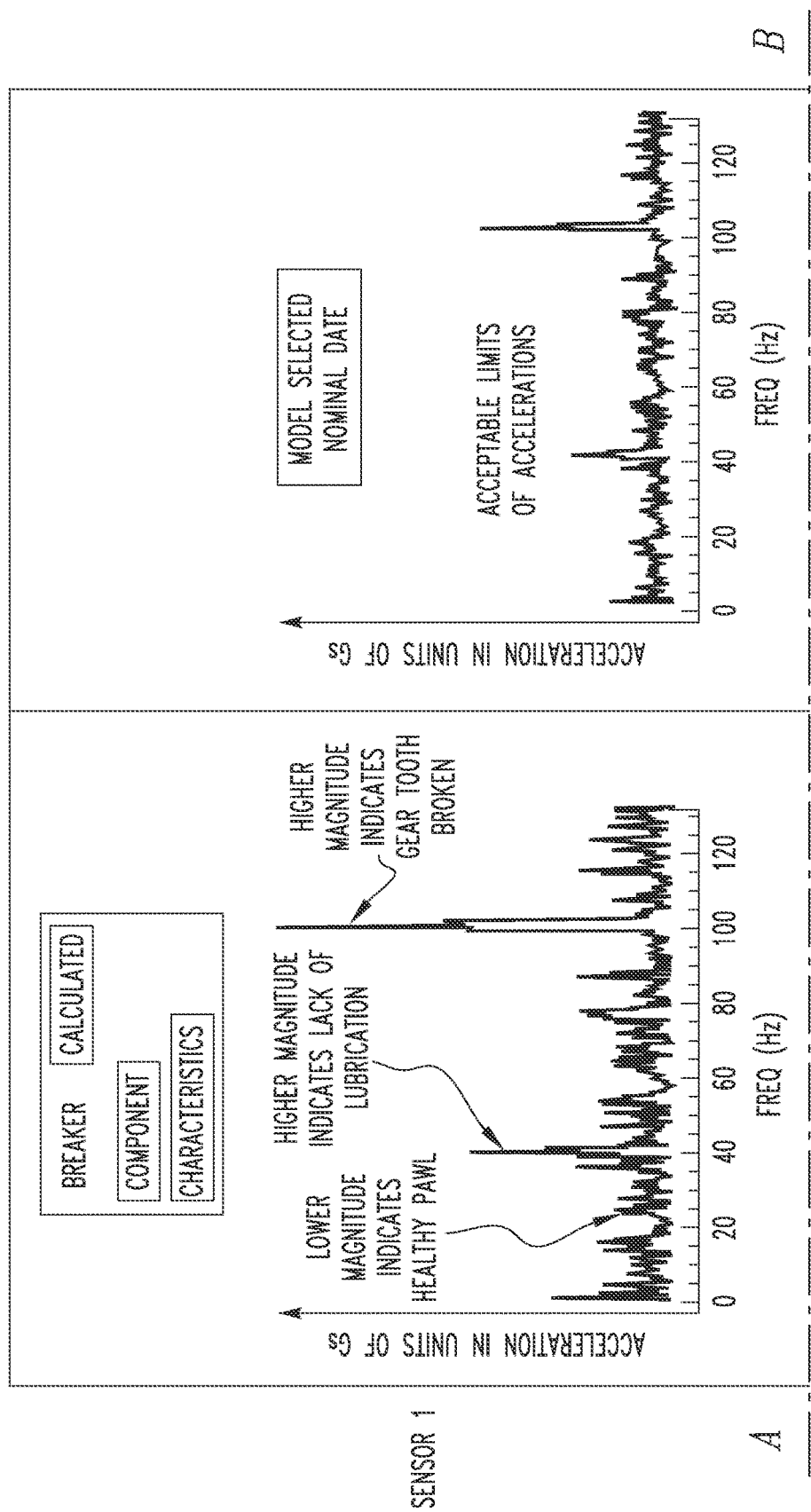
FIG. 18A is a visual representation of a comparison of calculated component characteristics to model selected nominal data for a first and second sensor assembly for a first sensor.
Figure 18B:
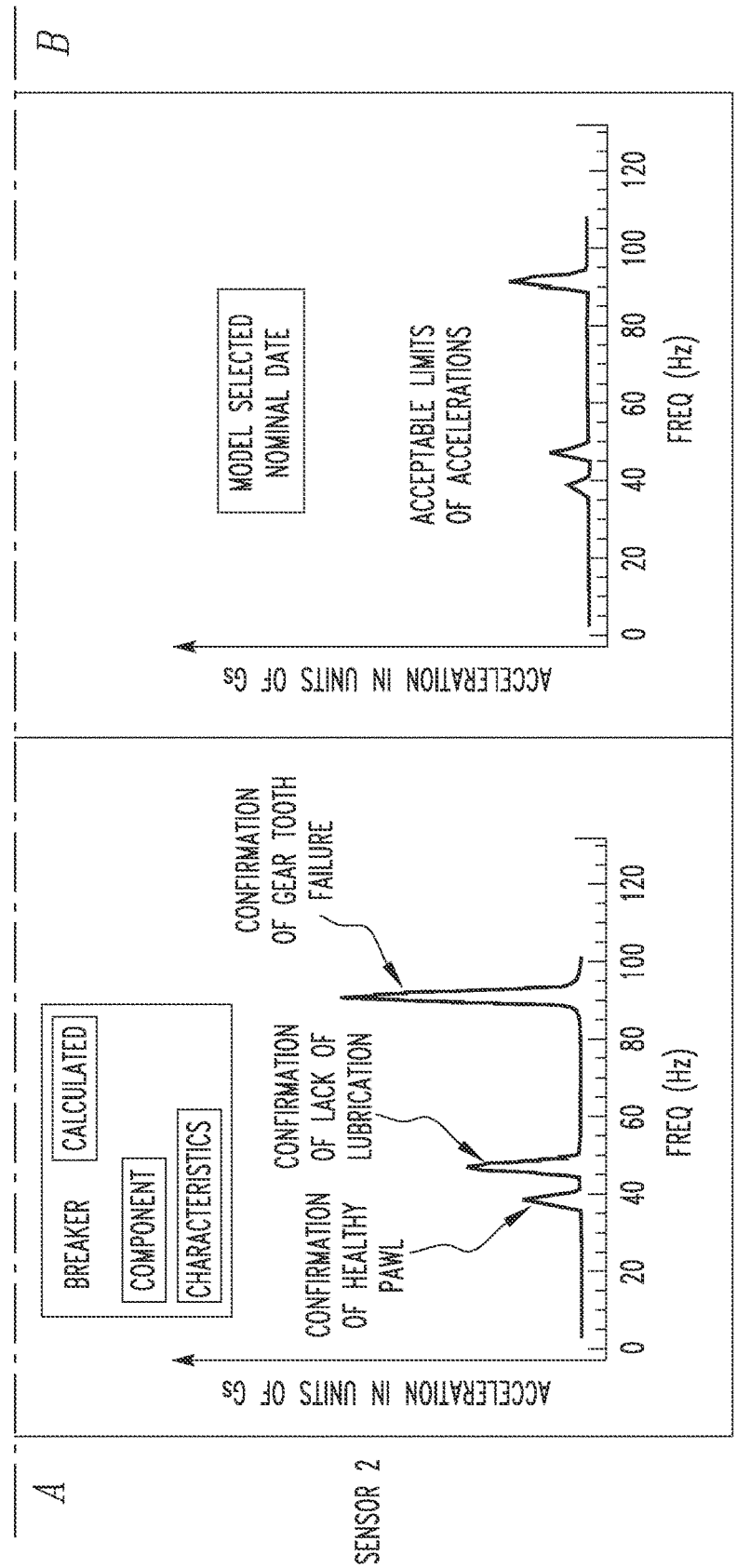
FIG. 18B is a visual representation of a comparison of calculated component characteristics to model selected nominal data for a first and second sensor assembly for a second sensor.

A visual representation of a comparison of the calculated component characteristics to the model selected nominal data for both a first and second sensor assembly 320, 320' is shown in FIGS. 18A-B (signal from third sensor assembly 320" is not shown). Further, as shown, the chronological position (on the figure) of a calculated component characteristic is associated with a particular operating mechanism components 28. Thus, when any calculated component characteristic is unacceptable relative to the corresponding attribute at a specific chronological position, the unacceptable calculated component characteristic indicates an associated operating mechanism component 28 needs attention. That is, the vibrations that occur during a specific operation, e.g. charging the closing spring 90, are known to happen in a specific chronological order.

Figure 19:
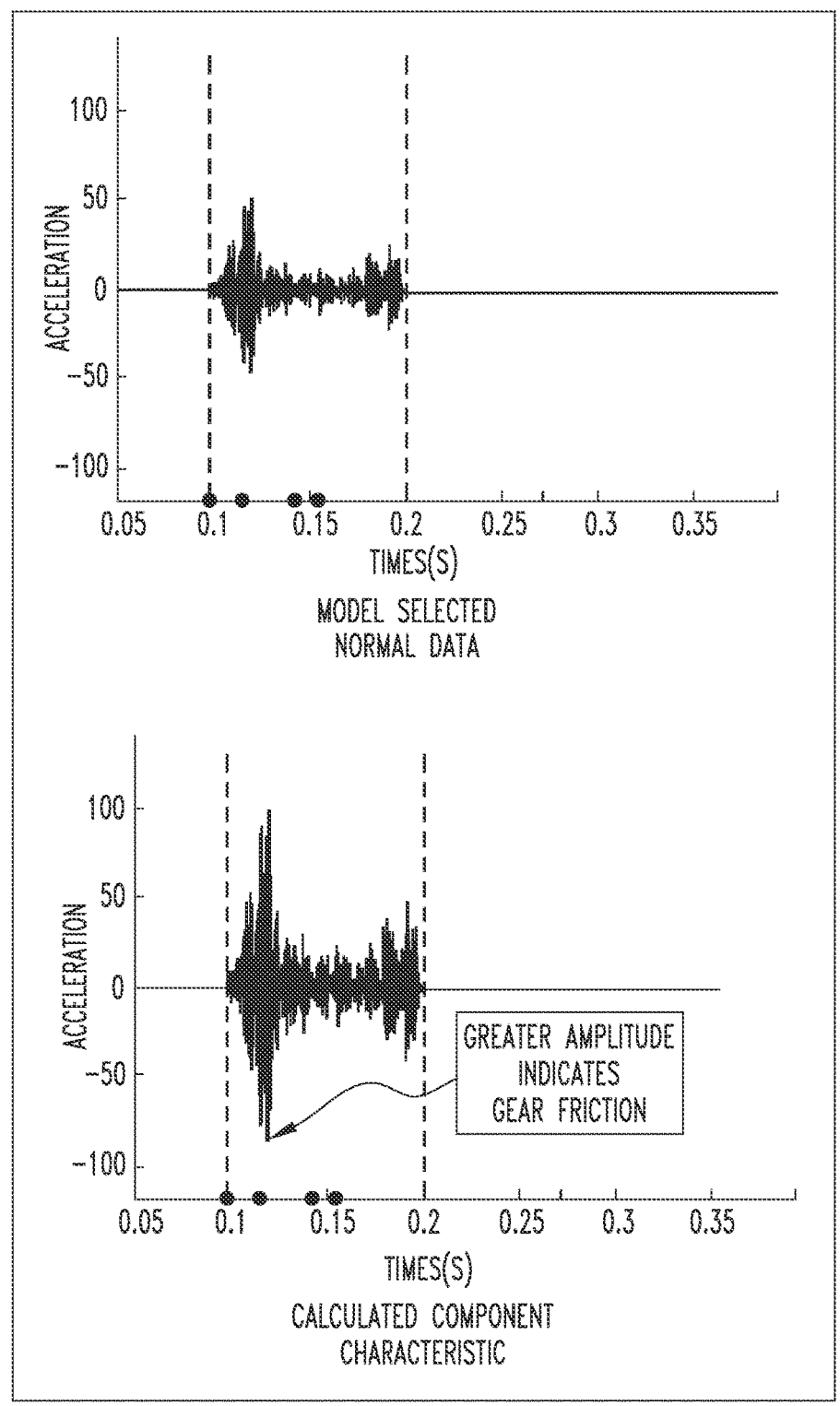
FIG. 19 is another visual representation of a comparison of calculated component characteristics to model selected nominal data.

If a calculated component characteristic for a vibration at a specific time in the sequence charging the closing spring 90 is unacceptable, the comparison assembly 230 is structured to identify an operating mechanism component 28 associated with that vibration, i.e. the vibration at a specific time. For example, as shown in FIG. 19, a vibration of a certain magnitude at about 0.16 seconds is associated with unacceptable gear friction. Thus, the comparison assembly 230 is structured to associate each data segment with a selected component of the circuit breaker assembly 10.

If any calculated component characteristic is unacceptable relative to the corresponding attribute, the comparison assembly 230 is structured to suggest a corrective action and/or identify a potential problem. It is understood that such suggestions are provided on the output assembly 240. Further it is noted that the Fourier transform is, in an exemplary embodiment, to find outlier data which causes extra frequency components.

The embodiment utilizing a number of vibration sensor assemblies 320 is also structured to determine the displacement of the contact assemblies 20, 22 during opening and closing operations. As used herein, "displacement of the contact assemblies" 20, 22 includes at least two characteristics of the movable contact 20; position and velocity. Further, the position of the movable contact 20 relative to the stationary contact 22 is a characteristic identified as "separation," i.e the distance between the contact assemblies 20, 22.

Figure 20:
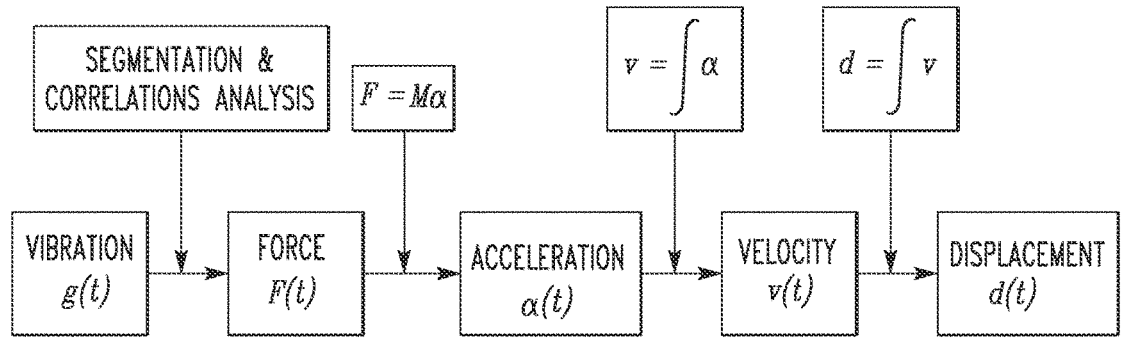
FIG. 20 is a model to estimate displacement curve from vibration data.

That is, in this embodiment, the "actual component characteristic output data" (discussed above) is used to estimate the displacement of the contact assemblies 20, 22. Broadly, the model for estimating a contact displacement curve from actual vibration output data is shown in FIG. 20. Further, for a closing operation, as represented in FIG. 17, the acceleration of movable contact 20 during segment t1 is assumed to be constant due to the bias of closing spring 90 and contact spring 94. During an opening operation, the acceleration of movable contact 20 during segment t1 is assumed to be constant due to the bias of opening spring 92 and contact spring 94. During segments t2 and t3 of a closing operation, acceleration is negative due to the dampening effect of a damper (not shown). Thus, given the model shown in FIG. 20, correlation analysis is used to find the relationship between approximated constant acceleration and vibration data. In an exemplary embodiment, acceleration is estimated from a linear relation to the vibration energy in each segment during which the movable contact 20 is moving. This is, in an exemplary embodiment, represented by the equation:

$$a = kE$$

Where a is the (approximated) acceleration to be estimated, E is the vibration energy in that segment, and k is the correlation coefficient between energy and acceleration, and E is derived by the square sum of vibration signal as follows;

$$E = \alpha \Sigma v(t)^2.$$

The coefficient $\alpha$ is equivalent to the mass of the movable contact assembly 20 and, in an exemplary embodiment, is measured in kilograms The correlation coefficient k is determined by experimentation on a masterpiece circuit breaker, as follows:

1. Setting a masterpiece circuit breaker in normal condition. Install vibration sensor(s) at a selected, fixed location.
2. Operating the circuit breaker to open and close. Using the circuit breaker displacement and velocity measurement instruments to record the displacement and velocity of the movable contact assembly 20.
3. Calculate the acceleration curve from the measured velocity, and compare the acceleration curve to the energy curve measured from vibration.
4. Select a point with same interval between maximum and minimum of velocity curve a(t), obtain the corresponding points on energy curve, and use minimum square error criteria to calculate the coefficient k between a(t) and E(t).

It is noted that correlation coefficient k is numeral based upon an exemplary relationship between $\alpha$ and E, as determined by experiment on a masterpiece circuit breaker. Correlation coefficient k is not limited to the linear relationship between $\alpha$ and E. The relationship is, in exemplary embodiments, $\alpha \sim \sqrt{E}$ or $a \sim k_1 E + k_2 E^2 + \ldots$.

The acceleration is used to determine a displacement estimation according to the equation:

$$D(t) = \int_o^t \int_o^y a(x) dx dy$$

Figure 21:
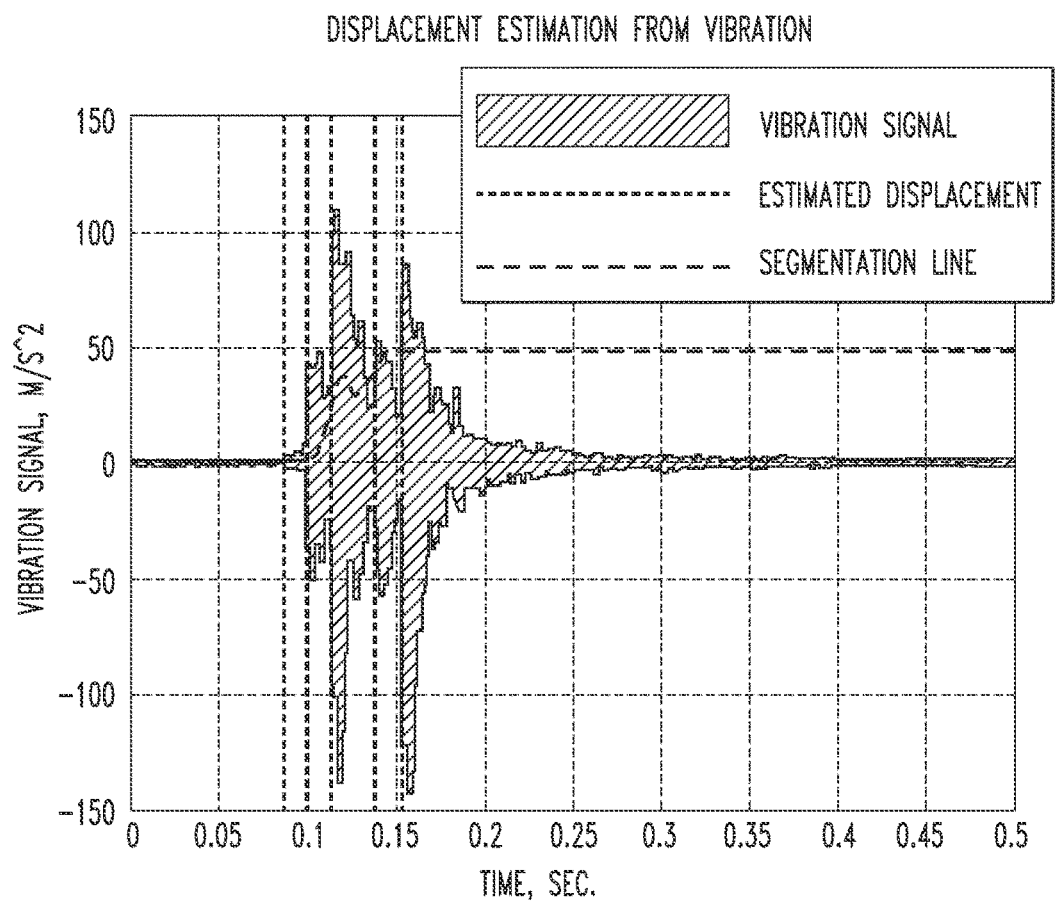
FIG. 21 is a graph of exemplary model selected nominal vibration data with a line representing estimated displacement.
Figure 22:
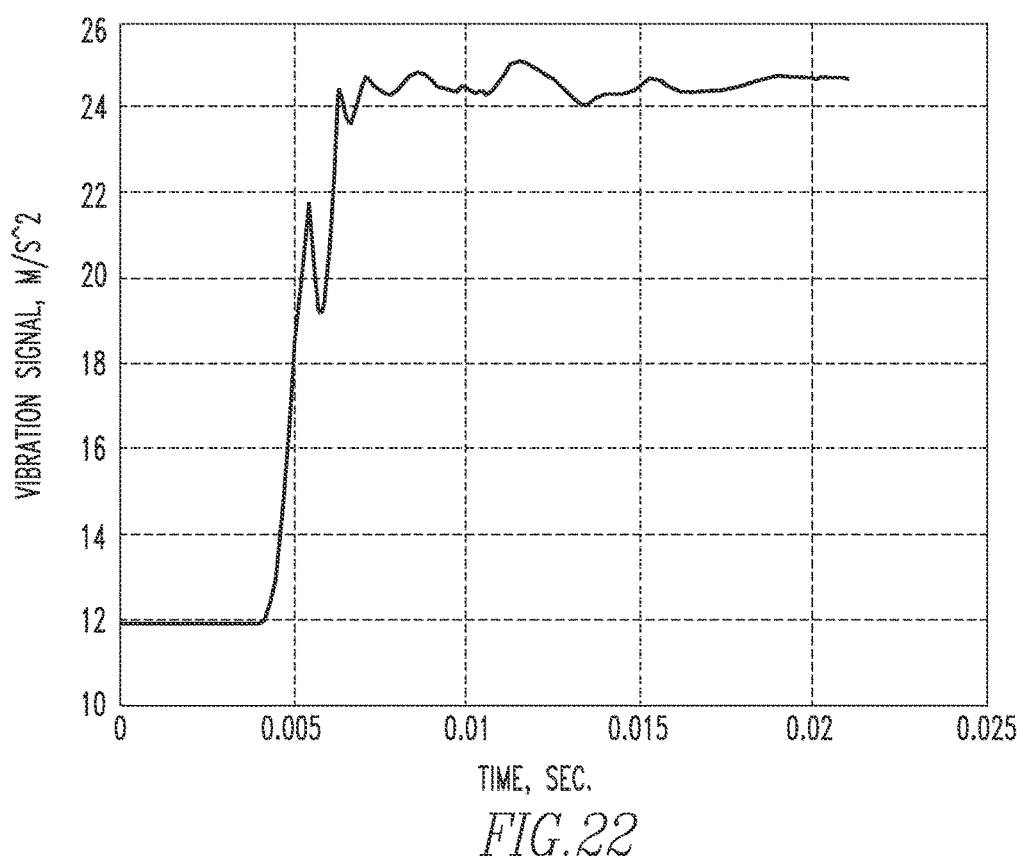
FIG. 22 is a graph representing a Closing Displacement Characteristic.

The method discussed above is then used to create a "Closing Displacement Characteristic." As used herein, a "Closing Displacement Characteristic" means the displacement of electrode when circuit breaker closes characterized by the closing velocity, the closing time, and selected parameters derived from displacement and time, such as, but not limited to, overshoot, rebound, and instantaneous velocity at closing point. For example, FIG. 21 shows a displacement estimation determined as described above. That data is then used to generate the Closing Displacement Characteristic as shown in FIG. 22.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of invention which is to be given the full breadth of the claims appended and any and all equivalents thereof.

What is claimed is:

1. A circuit breaker assembly comprising:
  a housing assembly;
  a number of components, each component having a number of characteristics;
  said number of components disposed in said housing assembly;
  said number of components including an operating mechanism;
  a number of vibration sensor assemblies;
  said operating mechanism includes a component monitoring system;
  wherein said number of vibration sensor assemblies are part of said component monitoring system;
  said component monitoring system includes a record assembly;
  said record assembly including selected nominal data for a selected circuit breaker component;
  wherein the selected nominal data is defined as a range or as a coefficient;
  said component monitoring system includes a comparison assembly;
  said comparison assembly including a processing assembly, an input/output device, and a comparison module;
  wherein said comparison assembly is structured to compare the actual component characteristics and the selected nominal data so as to determine the remaining useful life for a selected circuit breaker component;
  wherein said processing assembly is structured to execute said comparison module;

wherein said processing assembly is not a general purpose computer;
wherein said comparison assembly is structured to compare said vibration sensor assembly actual component characteristic output data to said selected nominal data and to determine the remaining useful life for a selected circuit breaker component;
said selected nominal data is model selected nominal data including segmented signal data;
said segmented signal data includes a number of data segments;
each data segment including a total energy attribute, a segment mean energy attribute, a segment duration attribute, and a time domain correlation attribute;
said comparison assembly is structured to divide said actual component characteristic output data into measured periods corresponding to said segmented signal data segments;
wherein said measured periods correspond to a cam and a roller impact, a collision and reduction of velocity to zero of a contact assembly, and, an oscillation of a spring;
said comparison assembly is structured to calculate calculated component characteristics including a total energy characteristic, a segment mean energy characteristic, a segment duration characteristic, and a time domain correlation characteristic;
wherein said comparison assembly is structured to compare said calculated component characteristics for each said measured period to the model selected nominal data for a corresponding segmented signal data segment; and
wherein said comparison assembly is structured to compare, within each measured period and segmented signal data segment, said total energy characteristic to said total energy attribute, said segment mean energy characteristic to said segment mean energy attribute, said segment duration characteristic to said segment duration attribute, and said time domain correlation characteristic to said time domain correlation attribute.

2. The circuit breaker assembly of claim 1 wherein each of said total energy attribute, segment mean energy attribute, segment duration attribute, and time domain correlation attribute are calculated by methods such as Fast Fourier transform (FFT), Short-time Fourier transform (STFT), Dynamic Time Warping (DTW) data.

* * * * *